US012354723B2

(12) United States Patent
Paulett et al.

(10) Patent No.: US 12,354,723 B2
(45) Date of Patent: Jul. 8, 2025

(54) SYSTEM AND METHOD FOR RADIOLOGY REPORTING

(71) Applicant: RAD AI, Inc., Berkeley, CA (US)

(72) Inventors: John Paulett, Berkeley, CA (US); William Boonn, Berkeley, CA (US); Woojin Kim, Berkeley, CA (US); Jeffrey Chang, Berkeley, CA (US); Doktor Gurson, Berkeley, CA (US)

(73) Assignee: RAD AI, Inc., San Francisco, CA (US)

( * ) Notice: Subject to any disclaimer, the term of this patent is extended or adjusted under 35 U.S.C. 154(b) by 0 days.

(21) Appl. No.: 18/638,368

(22) Filed: Apr. 17, 2024

(65) Prior Publication Data

US 2024/0347156 A1 Oct. 17, 2024

Related U.S. Application Data

(60) Provisional application No. 63/510,250, filed on Jun. 26, 2023, provisional application No. 63/496,521, filed on Apr. 17, 2023.

(51) Int. Cl.
| | | |
|---|---|---|
| *G16H 15/00* | (2018.01) | |
| *G06F 40/289* | (2020.01) | |
| *G16H 30/20* | (2018.01) | |
| *G16H 30/40* | (2018.01) | |

(52) U.S. Cl.
CPC ............ *G16H 15/00* (2018.01); *G16H 30/20* (2018.01); *G16H 30/40* (2018.01)

(58) Field of Classification Search
CPC ......... G16H 15/00; G16H 30/20; G16H 30/40
See application file for complete search history.

(56) References Cited

U.S. PATENT DOCUMENTS

| | | |
|---|---|---|
| 10,127,662 B1 | 11/2018 | Reicher et al. |
| 10,140,421 B1 | 11/2018 | Bernard et al. |
| 10,667,794 B2 | 6/2020 | Beymer et al. |
| 11,064,902 B2 | 7/2021 | Wallace et al. |
| 11,069,432 B2 | 7/2021 | Guo et al. |
| 11,164,045 B2 | 11/2021 | Paik et al. |
| 11,263,749 B1 | 3/2022 | Purushottam et al. |
| 11,342,055 B2 | 5/2022 | Chang et al. |

(Continued)

FOREIGN PATENT DOCUMENTS

| | | |
|---|---|---|
| CN | 111414464 A | 7/2020 |
| CN | 116364227 A | 6/2023 |

(Continued)

OTHER PUBLICATIONS

"Improving and automating lung cancer screening", Nuance, Data Sheet, Nov. 2020, https://www.nuance.com/asset/en_us/collateral/healthcare/data-sheet/ds-powerscribe-lung-cancer-screening-en-US.pdf.

(Continued)

*Primary Examiner* — Maroun P Kanaan
(74) *Attorney, Agent, or Firm* — Jeffrey Schox; Ivan Wong

(57) ABSTRACT

A method for radiology reporting includes any or all of: determining a set of inputs, determining a template, generating a radiology report, processing the radiology report, adjusting the radiology report, and/or any other suitable steps. A system for radiology reporting includes and/or interfaces with any or all of: a set of models, a computing system, a set of databases, a user interface, user devices, and/or any other suitable system components.

18 Claims, 17 Drawing Sheets

(56) References Cited

U.S. PATENT DOCUMENTS

| | | | |
|---|---|---|---|
| 11,380,432 | B2 | 7/2022 | Glottmann et al. |
| 11,475,358 | B2 | 10/2022 | Edgar et al. |
| 11,610,667 | B2 | 3/2023 | Gurson et al. |
| 11,615,890 | B2 | 3/2023 | Chang et al. |
| 11,803,759 | B2 | 10/2023 | Hu et al. |
| 12,032,658 | B2 | 7/2024 | Kiraly et al. |
| 2003/0154085 | A1 | 8/2003 | Kelley |
| 2007/0078679 | A1 | 4/2007 | Rose |
| 2010/0138239 | A1 | 6/2010 | Reicher et al. |
| 2013/0290031 | A1 | 10/2013 | Kay et al. |
| 2014/0379378 | A1 | 12/2014 | Cohen-Solal et al. |
| 2015/0112725 | A1 | 4/2015 | Ryan |
| 2015/0348229 | A1 | 12/2015 | Aguirre-Valencia et al. |
| 2016/0364862 | A1 | 12/2016 | Reicher et al. |
| 2018/0060533 | A1 | 3/2018 | Reicher et al. |
| 2018/0330828 | A1 | 11/2018 | Hayter |
| 2019/0021677 | A1 | 1/2019 | Grbic et al. |
| 2019/0122073 | A1 | 4/2019 | Ozdemir et al. |
| 2019/0139218 | A1 | 5/2019 | Song et al. |
| 2019/0156947 | A1 | 5/2019 | Nakamura et al. |
| 2019/0362835 | A1 | 11/2019 | Sreenivasan et al. |
| 2020/0226481 | A1 | 7/2020 | Sim et al. |
| 2020/0311613 | A1 | 10/2020 | Ma et al. |
| 2020/0334416 | A1 | 10/2020 | Manu et al. |
| 2020/0342967 | A1 | 10/2020 | Bronkalla et al. |
| 2020/0380675 | A1 | 12/2020 | Golden et al. |
| 2021/0005297 | A1 | 1/2021 | Oez |
| 2021/0035015 | A1 | 2/2021 | Edgar et al. |
| 2021/0090694 | A1* | 3/2021 | Colley ................. G16H 15/00 |
| 2021/0110912 | A1 | 4/2021 | Mukherjee |
| 2021/0216822 | A1 | 7/2021 | Paik et al. |
| 2021/0217535 | A1 | 7/2021 | Tahmasebi Maraghoosh et al. |
| 2021/0327596 | A1 | 10/2021 | Tahmasebi Maraghoosh et al. |
| 2021/0334462 | A1 | 10/2021 | Kukreja et al. |
| 2022/0020495 | A1 | 1/2022 | Sadeghi |
| 2022/0051771 | A1* | 2/2022 | Lyman ................. G06T 7/0014 |
| 2022/0059200 | A1 | 2/2022 | Rahbar et al. |
| 2023/0145535 | A1 | 5/2023 | Hatamizadeh et al. |
| 2023/0289529 | A1* | 9/2023 | Alikaniotis ........... G06F 40/211 |
| 2024/0266074 | A1 | 8/2024 | Smurro |
| 2024/0347156 | A1 | 10/2024 | Paulett et al. |

FOREIGN PATENT DOCUMENTS

| | | |
|---|---|---|
| CN | 117558439 A | 2/2024 |
| CN | 117995344 A | 5/2024 |
| CN | 118070227 A | 5/2024 |
| EP | 3246836 A1 | 11/2017 |
| WO | 0239415 A2 | 5/2002 |
| WO | 2019025601 A1 | 2/2019 |
| WO | 2020043673 A1 | 3/2020 |
| WO | 2020214683 A1 | 10/2020 |
| WO | 2022162167 A1 | 8/2022 |
| WO | 2022212771 A2 | 10/2022 |

OTHER PUBLICATIONS

"Lung Cancer Orchestrator", Philips, first downloaded May 19, 2023, https://www.usa.philips.com/healthcare/product/HC841017/lung-cancer-orchestrator.

"Lung Cancer Screening", Eon Health, first downloaded May 19, 2023, https://eonhealth.com/lung-cancer-screening-software/.

"Merge Announces Release of Fusion PACS MX(TM) 3.0 Featuring Integrated Digital Mammography, and Release of Merge Mammo(TM) 7.10", Business Wire, May 19, 2008, p. NA. ProQuest. Web. Aug. 29, 2023. (Year: 2008).

"PowerScribe One for radiology reporting, Next-generation radiology reporting", Nuance, https://www.nuance.com/healthcare/diagnostics-solutions/workflow-radiology-reporting/powerscribe-one.html#, first downloaded Mar. 11, 2024.

"Radiology reports designed for patients", Scanslated, first downloaded May 19, 2023, https://scanslated.com.

Agarwal, Sheela, et al., "Beyond the impression: How AI-driven clinical intelligence transforms the radiology experience", Radiology Business Journal sponsored webinar, Nov. 16, 2022.

Chang, Jeffrey, et al., "Method and System for the Computer-Assisted Implementation of Radiology Recommendations", U.S. Appl. No. 18/215,354, filed Jun. 28, 2023.

Dai, Ning, et al., "Style transformer: Unpaired text style transfer without disentangled latent representation", Ithaca: Cornell University Library, arXiv.org. (Year: 2019).

Deng, Mingkai, "RLPrompt: Optimizing Discrete Text Prompts with Reinforcement Learning", Machine Learning, Carnegie Mellon University, published Feb. 24, 2023.

Ebesu, Travis Akira, "Deep learning for recommender systems", (Order No. 13900137). Available from ProQuest Dissertations & Theses Global. (2293976827). (Year: 2019).

Garud, Hrishikesh Deepak, et al., "Transforming human pose forecasting", (Order No. 27814956). Available from ProQuest Dissertations & Theses Global. (2399247743). (Year: 2019).

Jettaku, Amarin, et al., "Relation extraction between bacteria and biotopes from biomedical texts with X attention mechanisms and domain-specific contextual representations", BMC Bioinformatics, 20, 1-17, (2019).

Koncel-Kedziorski, Rik, et al., "Understanding and generating multi-sentence texts", (Order No. 13814316). Available from ProQuest Dissertations & Theses Global. (2305944561). (Year: 2019).

Lambert, Nathan, et al., "Illustrating Reinforcement Learning from Human Feedback (RLHF)", Hugging Face, https://huggingface.co/blog/rlhf, published Dec. 9, 2022.

Lou, Robert, et al., "Automated detection of radiology reports that require follow-up imaging using natural language processing feature engineering and machine learning classification", Journal of digital imaging, 33(1), 131-136. (Year: 2020).

Lu, Edward, et al., "Lora: Low-Rank Adaptation of Large LANGuage Models", arXiv:2106.09685, https://doi.org/10.48550/arXiv.2106.09685, Jun. 17, 2021.

Malhotra, Tanya, "Exploring The Differences Between ChatGPT/GPT-4 and Traditional Language Models: The Impact of Reinforcement Learning from Human Feedback (RLHF)", MarkTestPost, https://www.marktechpost.com/2023/03/21/exploring-the-differences-between-chatgpt-gpt-4-and-traditional-language-models-the-impact-of-reinforcement-learning-from-human-feedback-rlhf/, Mar. 21, 2023.

Nandhakumar, Nidhin, et al., "Clinically Significant Information Extraction from Radiology Report", DocEng '17: Proceedings of the 2017 ACM Symposium on Document Engineering, Aug. 2017, pp. 153-162.

Paulett, John, et al., "System and Method for Radiology Reporting", U.S. Appl. No. 18/638,368, filed Apr. 17, 2024.

Sanjabi, Nima, "Abstractive text summarization with attention-based mechanism", (Projecte Final de Master Oficial). UPC, Facultat d'Informatica de Barcelona. (Year: 2018).

Sean, Xiao, "Fine-tuning LLMs Made Easy with LoRA and Generative AI-Stable Diffusion LoRA", Medium, https://xiaosean5408.medium.com/fine-tuning-llms-made-easy-with-lora-and-generative-ai-stable-diffusion-lora-39ff27480fda, Mar. 11, 2023.

Song, Huan, "Data-driven representation learning in multimodal feature fusion", (Order No. 10838232). Available from ProQuest Dissertations & Theses Global. (2094858110). (Year: 2018).

Van Veen, Dave, et al., "RadAdapt: Radiology Report Summarization via Lightweight Domain Adaptation of Large Language Models", arXiv:2305.01146, https://doi.org/10.48550/arXiv.2305.01146, May 2, 2023.

Witteveen, Sam, "Building a Summarization System with LangChain and GPT-3—Part 2", https://www.youtube.com/watch?v=d-yeHDLgKHw, Mar. 11, 2023.

Xue, Y., et al., "Multimodal Recurrent Model with Attention for Automated Radiology Report Generation", Medical Image Computing and Computer Assisted Intervention—MICCAI 2018. MICCAI 2018. Lecture Notes in Computer Science, vol. 11070. Springer, Cham. https://doi.org/10.1007/978-3-030-00928-1_52 (Year: 2018).

Yao, Shunyu, et al., "ReAct: Synergizing Reasoning and Acting in Language Models", https://react-lm.github.io, Oct. 6, 2022.

(56) References Cited

OTHER PUBLICATIONS

Zech, John, et al., "Natural Language-based Machine Learning Models for the Annotation of Clinical Radiology Reports", Radiology Reports. Jan. 30, 2018 (Jan. 30, 2018).

Zhang, Yuhao, et al., "Learning to Summarize Radiology Findings", Oct. 8, 2018 (Oct. 8, 2018). 1-20 [retrieved on Nov. 18, 2020].

Chang, et al., "Method and System for the Computer-Aided Processing of Medical Images", U.S. Appl. No. 18/952,233, filed Nov. 19, 2024.

Chang, et al., "System and Method for Automatically Displaying Information at a Radiologist Dashboard", U.S. Appl. No. 18/952,147, filed Nov. 19, 2024.

Li, et al., "BLIP-2: Bootstrapping Language-Image Pre-training with Frozen Image Encoders and Large Language Models", arXiv:2301.12597v1, Jan. 30, 2023.

Xu, et al., "ELIXR: Towards a general purpose X-ray artificial intelligence system through alignment of large language models and radiology vision encoders", arXiv:2308.01317 [cs. Cv], Aug. 2, 2023.

* cited by examiner

S100 ⟶

142 ⟶

MR Knee wo IV Contrast  Calrissian, Lando 43y M  Right knee pain
Acc: R1AT2UH155  MRN: 74412341  Site: John Peter Smith
DOB: 1979-10-30  Ordering: McCoy, Leonard

51 ⟶

EXAM:
MR Knee wo IV Contrast
HISTORY:
Right knee pain
TECHNIQUE:
Multi-planar, multi-sequence MR imaging of the knee was performed using routine protocol without contrast.
COMPARISON:
FINDINGS:
BONES: Normal marrow signal. No fracture, neoplasm, or osteonecrosis.
SOFT TISSUES: No abnormal masses or fluid collections.
JOINT: No effusion or malalignment.
CARTILAGE: No focal defects.
LATERAL MENISCUS: Intact.
MEDIAL MENISCUS: Complex, predominantly horizontal medial meniscal tear involving the body and posterior horn with associated parameniscal cyst formation.
ANTERIOR CRUCIATE LIGAMENT: Intact.

PRIORS  DOCUMENT TREE
No priors

Study — MR Knee wo IV Contrast (R1AT2UH155) RPID522 Completed  ⊕ Associated Exams — 40

Omni — IMPRESSION  UNCHANGED — 141

Macros
User | Global  All Template Macro
⊕ = MRI Knee
⊕ = Additional Support
⊕ = Atelectasis
⊕ = Blunting
⊕ = Bone Short
⊕ = CT Abdomen
⊕ = Chest
⊕ = Chest ICU
⊕ = Chest Short
⊕ = Communication
⊕ = Endotracheal
⊕ = Enteric

MR Knee wo IV Contrast  Calrissian, Lando 43y M  Right knee pain
Acc: R1AT2UH155  MRN: 74412341  Site: John Peter Smith
DOB: 1979-10-30  Ordering: McCoy, Leonard

30 ⟶

SOFT TISSUES: No abnormal masses or fluid collections.
JOINT: No effusion or malalignment.
CARTILAGE: No focal defects.
LATERAL MENISCUS: Intact.
MEDIAL MENISCUS: Complex, predominantly horizontal medial meniscal tear involving the body and posterior horn with associated parameniscal cyst formation.
ANTERIOR CRUCIATE LIGAMENT: Intact.
POSTERIOR CRUCIATE LIGAMENT: Intact.
MEDIAL COLLATERAL LIGAMENT: Possible MCL bursitis.
LATERAL COLLATERAL LIGAMENT: Intact.
EXTENSOR MECHANISM: Intact.
IMPRESSION:
1. Complex, predominantly horizontal medial meniscal tear involving the body and posterior horn with associated parameniscal cyst formation.
2. Possible MCL bursitis.

PRIORS  DOCUMENT TREE
No priors

Study — MR Knee wo IV Contrast (R1AT2UH155) RPID522 Completed  ⊕ Associated Exams — 40

Omni — IMPRESSION  UNCHANGED — 141

Macros
User | Global  All Template Macro
⊕ = MRI Knee
⊕ = Additional Support
⊕ = Atelectasis
⊕ = Blunting
⊕ = Bone Short
⊕ = CT Abdomen
⊕ = Chest
⊕ = Chest ICU
⊕ = Chest Short
⊕ = Communication
⊕ = Endotracheal
⊕ = Enteric

| XR Foot 3+ Views | Vader, Darh 72y M | Foot pain |
| Acc: RULV2UH1RE | MRN: 68247823 | Site: John Peter Smith |
| | DOB: 1950-04-21 | Ordering: McCoy, Leonard |

HISTORY: Foot pain
TECHNIQUE: Frontal, lateral, and oblique radiographs of the left foot were obtained.
COMPARISON: May 09, 2022
LIMITATIONS: None.
FINDINGS:
Severe Charcot deformity at the left ankle with talar collapse as well as previous midfoot fusion with multiple screws. No change in the alignment of the ankle or foot at this time.
IMPRESSION:
1. Severe Charcot deformity at the left ankle with talar collapse as well as previous midfoot fusion with multiple screws.
2. No significant change in the alignment of the ankle or foot since the prior study on May 09, 2022.
3. No acute fracture or dislocation identified.

PRIORS  DOCUMENT TREE

| 2022-05-09 RULV2UH1NE XR Foot3+ Views | HISTORY: Bilateral Charcot foot/ankle |
| | COMMENT: AP, Lateral and oblique views of the left foot. |
| | COMPARISON: January 3, 2022 |
| | IMPRESSION: images of the left foot show the severe Charcot deformity at the left ankle with talar collapse as well as previous midfoot fusion with multiple screws. There is no change in the alignment of the ankle or foot at this time. |

Study
 XR Foot 3+ Views
  (R1AT2UH155)
  RPID522 Routine
  Completed
 ⊕ Associated Exams Omni

[IMPRESSION]
[UNCHANGED]

Macros

User | Global   All Template Macro
⊕ = Bone Short
⊕ = Additional Support
⊕ = Atelectasis
⊕ = Blunting
⊕ = CT Abdomen
⊕ = Chest
⊕ = Chest ICU
⊕ = Chest Short
⊕ = Communication
⊕ = Endotracheal
⊕ = Enteric
⊕ = MRI Knee

FIGURE 7

HISTORY: elevated PSA

TECHNIQUE: Multiplanar, multisequence MR imaging of the pelvis and prostate was performed prior to and following intravenous administration of gadolinium-based contrast material.

COMPARISON: None.

FINDINGS:

43 → Prostate Measurements (AP x TV x CC): ☐ x ☐ x ☐ cm
Total Prostate Volume: ☐ ml Peripheral zone:

Central gland:

Seminal vesicles:

Capsule:

Neurovascular Bundles:

Rectoprostatic Angles:

Lymph nodes: .

ADDITIONAL FINDINGS:

PRIORS  DOCUMENT TREE

---

HISTORY: elevated PSA

TECHNIQUE: Multiplanar, multisequence MR imaging of the pelvis and prostate was performed prior to and following intravenous administration of gadolinium-based contrast material.

COMPARISON: None.

FINDINGS:

43 → Prostate Measurements (AP x TV x CC): [3.9] x [4.6] x [3.2] cm
44 → Total Prostate Volume: [30.06] ml Peripheral zone:

Central gland:

Seminal vesicles:

Capsule:

Neurovascular Bundles:

Rectoprostatic Angles:

Lymph nodes: .

ADDITIONAL FINDINGS:

PRIORS  DOCUMENT TREE

PROCEDURE: Frontal view of the chest.

HISTORY: Status post cardiac arrest on with subsequent intubation.

COMPARISON: 1/22/2023.

FINDINGS:

Tubes, lines, surgical material: Endotracheal tube in appropriate position.

Lungs and pleura: Low lung volumes with associated atelectasis. Stable bilateral severe airspace and interstitial markings, likely representing pulmonary edema, although superimposed pneumonia cannot be ruled out. No pleural effusions. No pneumothorax.

Cardiovascular and mediastinum: The cardiomediastinal silhouette is stable.

IMPRESSION:

Stable bilateral severe airspace and interstitial markings, likely representing pulmonary edema, although superimposed pneumonia cannot be ruled out.

Clinical indication: Shortness of breath.

Technique: PA and lateral views of the chest.

Comparison: 2/8/23.

Findings:

Mild pulmonary edema. Moderate right pleural effusion. No Pneumothorax

Cardiomediastinal silhouette is stable.

60 ⟶

Impression:

1. Mild pulmonary edema. Moderate right pleural effusion.

FIGURE 12

History: Coronary risk stratification.

Technique: Unenhanced ECG-triggered CT of the heart was performed.

Comparison: None.

FINDINGS:

CORONARY CALCIUM SCORE:

| Vessel | Number of Calcifications | Calcium volume | Calcium Score (Agatston) |
|---|---|---|---|
| LM: | 0 | 2 | 34 |
| LAD: | 0 | 6 | 0 |
| LCX: | 0 | 0 | 0 |
| RCA: | 0 | 0 | 0 |
| Total: | 0 | 8 | 34 |

The lungs are clear.

The heart is normal in size.

Additional findings: none

IMPRESSION:

Total coronary calcium score is 34. Total calcium volume is 8. Total number of coronary artery calcifications is 0. For a male patient aged 36y, this corresponds to the Age out of range percentile, that is, . By Rumberger criteria, this corresponds to a moderate cardiovascular risk.

Prostate Measurements (AP x TV x CC): 5 x 7 x 8 cm

Total Prostate Volume: 146.6 ml

FIGURE 13

SYSTEM AND METHOD FOR RADIOLOGY REPORTING

CROSS-REFERENCE TO RELATED APPLICATIONS

This application claims the benefit of U.S. Provisional Application No. 63/510,250, filed 26 Jun. 2023, and U.S. Provisional Application No. 63/496,521, filed 17 Apr. 2023, each of which is incorporated in its entirety by this reference.

TECHNICAL FIELD

This invention relates generally to the radiology field, and more specifically to a new and useful system and method for radiology reporting in the radiology field.

BRIEF DESCRIPTION OF THE FIGURES

FIG. 6B-6C depict an illustrative example of a report generated based on findings (e.g., the findings in 6A).

FIG. 7 depicts an illustrative example of the system generating an unchanged radiology report.

FIG. 8 depicts an illustrative example of performing field calculations within a template and/or macro.

FIG. 9B depicts an illustrative example of a prior radiology report.

FIG. 12 depicts an illustrative example of generating a findings section that includes a dropdown menu.

FIG. 13 depicts an illustrative example of generating a findings section that includes a table.

DETAILED DESCRIPTION

The following description of the embodiments of the invention is not intended to limit the invention to these embodiments, but rather to enable any person skilled in the art to make and use this invention.

1. Overview

Figure 1:
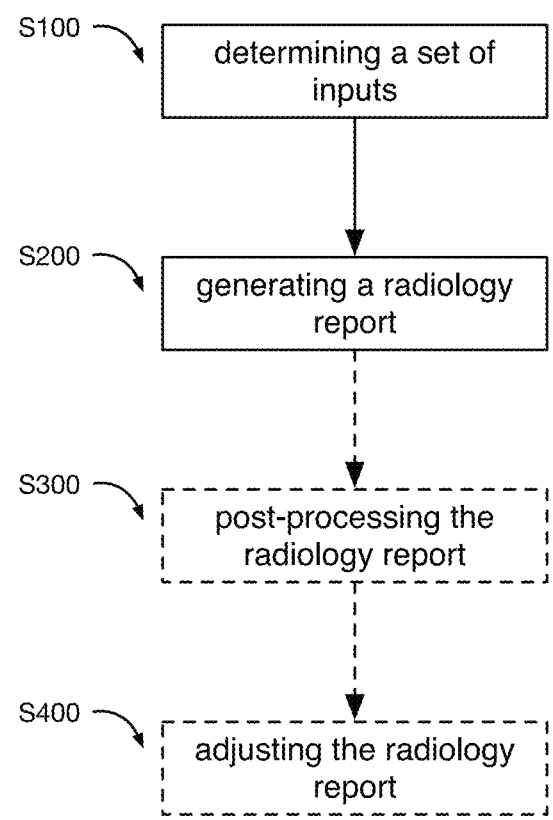
FIG. 1 is a schematic representation of a variant of the method.

As shown in FIG. 1, the method can include: determining a set of inputs S100 and generating a radiology report S200. However, the method can additionally or alternatively include any other suitable steps.

In variants, the method can function to generate a radiology report (e.g., a complete radiology report) from a set of inputs. For example, the method can function to generate a radiology report with minimal or no manual inputs from a radiologist.

2. EXAMPLES

In an example, all or a portion of a radiology report can be generated based on a set of inputs (e.g., dictated findings, automatically determined inputs, current and/or prior study information, patient information, relevant templates and/or macros, etc.). The radiology report can be generated automatically (e.g., in a zero-click fashion) and/or based on a user action (e.g., a minimal user action, less action than fully entering the information, etc.). In a specific example, the radiology report can be generated using customized language (e.g., using language models providing language customized to a radiologist, radiologist group, and/or other user identity). The radiology report can optionally be an initial radiology report draft that can then be modified (e.g., manually and/or automatically).

In a first specific example, an entire radiology report can be automatically generated with minimal (or no) input from a radiologist (e.g., without requiring the radiologist to dictate or otherwise input findings). A set of findings can be determined based on a set of inputs (e.g., including radiology images, patient history, etc.) using a set of models (e.g., image analysis models), which can be a part of the system for radiology reporting, or a part of an image analysis software (e.g., a third party image analysis software such as: HL7, FHIR, FHIRcast, API-based software, Rad AI Reporting SDK, etc.). Based on the set of findings, a full report (e.g., a draft) can be generated (e.g., using a set of trained models), optionally in a desired style (e.g., the style of the radiologist), and presented to the radiologist (e.g., upon opening the study associated with the report) for review, wherein the radiologist can sign off on and/or edit the report. Additionally or alternatively, a final report can be generated directly from a set of radiology images (e.g., without radiologist intervention or review) using a set of trained models (e.g., imaging analysis models and text generation models) as described herein, and optionally the generated report can be sent directly to an external system (e.g., RIS, PACS, EHR, etc.).

In a second specific example, the method can include selecting a template based on a first set of inputs (e.g., including patient history, study information, etc.), filling in the template based on a second set of inputs (e.g., including dictated findings, typed findings, etc.), and generating the report based on the first and second set of inputs.

In a third specific example, different report generation parameters can optionally be selected based on a user action (e.g., at a user interface). In a first illustrative example, a first user action (e.g., dictating "generate report", a button click, a hotkey press, etc.) can trigger generation of a complete radiology report, including findings and impressions, based on dictated findings (e.g., free-dictation). In a second illustrative example, a second user action (e.g., dictating "unchanged") can trigger generation of a radiology report, wherein all or most of the report is generated based on information in prior report(s), with minimal or no significant changes relative to the prior report(s). In a third illustrative example, a third user action (e.g., dictating "unchanged except . . . ") that includes content associated with one or more inputs (e.g., findings and/or changes relative to one or more prior reports) can trigger generation of a radiology report, wherein all or most of the report is generated based on those inputs as well as information in prior report(s).

3. Technical Advantages

Variants of the technology can confer one or more advantages over conventional technologies.

In current radiology workflows, one of the radiologist's main responsibilities is to identify and record his or her findings from the study (e.g., imaging, exam, etc.) in the radiology report. Currently, this typically requires manual dictation by the radiologist of each individual finding into radiology reporting software, manual dictation of language related to pertinent negative findings, comparison with reports from prior studies and manual dictation of comparison language, manual dictation of the clinical indication (e.g., the reason for the study) and imaging technique, manual calculation and classification of lesion sizes and characteristics, selection and insertion of a specific report template, and manual correction of any speech recognition errors or other report-related errors and omissions using either additional voice dictation or typed edits with a keyboard. Given that each radiologist typically dictates between 50 and 250 radiology reports per shift, radiologists spend the majority of their time manually dictating and manually correcting reports. This is a major contributor to radiologist fatigue and burnout, which is widely recognized as the most pressing issue facing the field of radiology. Imaging volumes across the US and worldwide continue to rise each year, and the number of radiologists remains relatively stable, meaning that each radiologist needs to dictate more studies each year.

First, variants of the technology can increase the efficiency of radiologist (and/or of any other medical professional) reporting. For example, variants of the technology can reduce the number of user actions and/or reduce time spent: analyzing images, dictating or otherwise inputting information, checking a medical document (e.g., a radiology report), editing a medical document (e.g., a radiology report), selecting a report template (e.g., out of a set of thousands of templates available to the medical professional), and/or performing any other reporting processes. In specific examples, variants of the technology can automatically import prior findings for a patient from previous imaging studies so that the radiologist only needs to enter new findings, rather than allocate time to filling out all findings within an imaging study.

Second, variants of the technology can increase the efficiency of a medical professional (e.g., a radiologist) reporting by enabling the medical professional to enter freeform inputs (e.g., via a dictation software), and automatically generating the medical document (e.g., radiologist report) without requiring the medical professional to spend time formatting and/or placing their inputs within different regions (e.g., sections) of the document. In examples, the medical professional can dictate and/or type their inputs (e.g., findings, notes, etc.) in an unstructured format into an input interface (e.g., microphone, text box, VR headset, etc.), and the system automatically sorts all entered information into appropriate fields within the medical document (e.g., into each of a set of fields for categories of findings within a template).

Third, variants of the technology can include implementing different report generation parameters (e.g., selecting different models and/or inputs to use) based on different radiologist triggers. This can enable using a more efficient (e.g., computationally efficient, efficient for the radiologist, etc.) and/or accurate method to generate the radiology report, tailored to the current study.

Fourth, variants of the technology can further reduce radiologist fatigue and errors by reducing a need for the radiologist to shift their attention between portions of the radiology report and/or other platforms (e.g., PACS). In a first example, variants of the technology can retrieve relevant case information (e.g., patient history) for a particular section of a report that a radiologist is working on, rather than traditional systems and methods which would require the radiologist to search for and retrieve relevant case information. In a second example, variants of the technology can perform error correction automatically, reducing a need for the radiologist to spend time reviewing for errors (e.g., calculation errors, grammatical errors, etc.) and/or inconsistencies. Corrected errors can optionally be surfaced to the radiologist (e.g., to receive confirmation to ensure accuracy), or the report can automatically be corrected without surfacing (e.g., highlighting, flagging, etc.) the corrections. In a third example, the system can include a unified input interface where a radiologist can perform multiple actions, such as requesting information, performing an error correction, asking a question about a patient's history, and/or any other suitable report generation or correction function, thereby reducing a need for the radiologist to navigate through multiple features of a radiology generation platform.

However, further advantages can be provided by the system and method disclosed herein.

4. System

Figure 14:
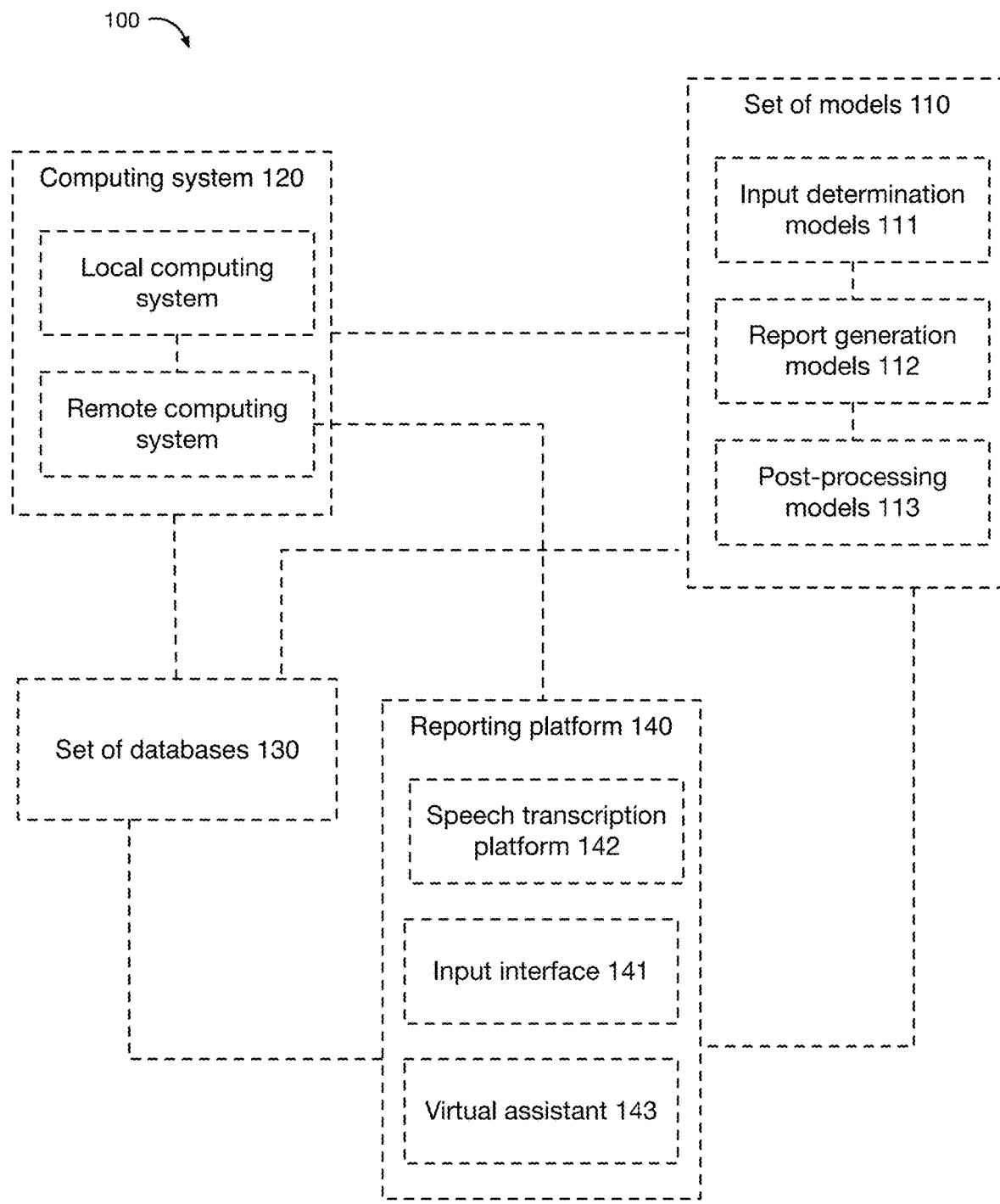
FIG. 14 is a schematic representation of a variant of the system.

As shown in FIG. 14, the system 100 can include and/or interface with any or all of: one or more models 110, a computing system 120, a set of databases 130, a user interface (e.g., referred to equivalently herein as an "input interface"), user devices, and/or any other suitable system components.

The computing system 120 can include one or more: CPUs, GPUs, custom FPGA/ASICS, processors, microprocessors, servers, cloud computing, storage; memory; and/or any other suitable components. The computing system can be local, remote, distributed, or otherwise arranged relative to any other system or module.

The system can include a set of one or more models 110, including input determination models 111, report generation models 112 (e.g., language model), post-processing models 113, and/or any other model. The models can include machine learning approaches, classical or traditional approaches, and/or be otherwise configured. The models can include regression, decision tree, LSA, clustering, association rules, dimensionality reduction, neural networks (e.g., CNN; DNN; CAN; LSTM; RNN (e.g., such as LSTM, GRU, etc.); FNN; encoders; decoders; deep learning models (e.g., Mamba); transformers; etc.), ensemble methods, optimization methods, classification, rules, heuristics, equations (e.g., weighted equations, etc.), selection (e.g., from a library), regularization methods (e.g., ridge regression), Bayesian methods (e.g., Naive Bayes, Markov), instance-based methods (e.g., nearest neighbor), kernel methods, support vectors (e.g., SVM, SVC, etc.), statistical methods (e.g., probability), comparison methods (e.g., ranking, similarity, matching, distance metrics, thresholds, etc.), deterministics, genetic programs, and/or any other suitable model. The models can include (e.g., be constructed using): a set of input layers (e.g., encoders), output layers (e.g., decoders such as beam search decoders), and/or hidden layers (e.g., connected in series, such as in a feed forward network; connected with a feedback loop between the output and the input, such as in a recurrent neural network; etc.; wherein the layer weights and/or connections can be learned through training); a set of connected convolution layers (e.g., in a CNN); attention mechanisms (e.g., sequence-to-sequence architecture; a set of attention layers and/or self-attention layers; etc.); and/or have any other suitable architecture.

In an example, the models can include one or more language models (e.g., large language models [LLMs]) configured for natural language processing (NLP). In a specific example, models can include: one or more transformers and/or transformer systems (e.g., Bidirectional Encoder Representations from Transformers [BERT], Generative Pre-Trained Transformer [GPT], etc.); a transformer with any suitable number and/or arrangement of encoders and decoders (e.g., arranged in a sequential and/or parallel arrangement); and/or any other suitable transformers or models. In a second specific example, models can include: one or more non-transformer based models (e.g., deep learning-based models such as Mamba, sequence modeling techniques, state space models, etc.); and/or any other large language models and/or other suitable models.

Models can be trained (e.g., pre-trained, retrained, tuned, fine-tuned, etc.), learned, fit, predetermined, untrained, and/or can be otherwise determined. The models can be trained or learned using: supervised learning, unsupervised learning, self-supervised learning, semi-supervised learning (e.g., positive-unlabeled learning), reinforcement learning, transfer learning, Bayesian optimization, fitting, interpolation and/or approximation, backpropagation, and/or otherwise generated. For example, models can be trained based on annotated radiology reports, manually generated radiology reports, synthesized radiology reports, labeled data, unlabeled data, positive training sets, negative training sets, and/or any other suitable set of data. Models can optionally be trained and/or undergo post-processing (e.g., in S300) using: an additional model (e.g., a first model is used to teach a second model), autonomous agents (e.g., while models interact with each other), and/or any other model interactions.

The system can include and/or interface with a set of databases 130 (e.g., EHR, EMR, RIS, CIS, PACS, etc.). Additionally or alternatively, the system can include and/or interface with: a reporting platform 140; a Picture Archiving and Communication System (PACS) and/or alternative image viewing and image storage platform; a speech recognition platform; a radiology worklist; a Radiology Information System (RIS); an electronic medical record (EMR) database; an electronic health record (EHR) database; a Clinical Information System (CIS) platform; a Health Information System (HIS) platform; a Laboratory Information System (LIS) platform; vendor-neutral archive (VNA) components; ontologies (e.g., radiological or other clinical ontology database); and/or any other database, storage, server, and/or software tools. In a specific example, the system includes a reporting platform (including a speech recognition platform and a user interface), wherein the reporting platform receives inputs and/or user actions from a radiologist, and displays a generated radiology report (e.g., determined using one or more models). In variants, the reporting platform 140 can include an input interface 141 (e.g., microphone, text box, etc.), which can function to receive input from a user (e.g., unstructured input), a speech transcription platform 142, and/or any other suitable components. The input interface can be rendered at a display of a user device (e.g., as shown in FIGS. 6A-6C, FIG. 7, FIG. 8, FIGS. 9A-9B, FIG. 10, FIG. 12, FIG. 13, etc.), part of an audio input device (e.g., the user device, microphone associated with speech-to-text software, etc.), include any combination of devices, and/or include any other device(s). In examples, the user device can include: a computer (e.g. a radiologist workstation computer), a headset (e.g., a virtual reality (VR) headset, an augmented reality (AR) headset, etc.), a mobile device (e.g., smartphone), and/or any other suitable device. Components of a user device can include a display subsystem (e.g., monitor, screen, projected image, etc.), an input subsystem (e.g., keys, touchscreen, microphone, etc.), one or more sensors (e.g., inertial measurement units, accelerometers, gyroscope, cameras, etc.), a processing subsystem, and/or any other suitable subsystem. Optionally, the system can include and/or interface with a software development kit, wherein customers and/or third parties can build additional features (e.g., further tools, features, functionality, analytics, historical report search, etc.) on top of the system (e.g., the reporting platform).

The system can include and/or interface with an optional reporting platform. The reporting platform can optionally include a virtual assistant 143 (e.g., chat bot, voice-based assistant, etc.), which can function to provide information to and/or receive information from a user. In variants, the virtual assistant can receive input from a user and determine an appropriate response. In examples, the virtual assistant can respond by: answering a user question, directing the user to information (e.g., contained within the report, linked to outside of the report, etc.), update an error within the generated report, and/or otherwise function. Additionally or alternatively, the virtual assistant 143 can determine a set of information to surface to and/or solicit from a user. In examples, the virtual assistant can surface information (e.g., via a notification) to a user, such as: an indication that an error has been corrected, a section of a report that requires further review, contact information of another medical professional (e.g., on the patient's care team, a specialist, a clinical trial coordinator, etc.) and/or any other entity (e.g., patient emergency contact information), and/or any other suitable information. In further examples, the virtual assistant can prompt a user to provide an input (e.g., as a response to information surfaced to the user), which can include a direct input to the report (e.g., fill out an incomplete section of a report), an input required for one or more models to run (e.g., to fill out an incomplete section of a report, to perform an error correction, etc.), a selection (e.g., a positive or a negative selection, a selection from a plurality of options, etc.) of one or more model outputs (e.g., a verification/rejection of an error correction performed by the system, a dropdown menu selection, etc.), and/or any other suitable input. Additionally or alternatively to a reporting platform, the system (e.g., the set of trained models) can integrate directly with one or more external systems (e.g., RIS, PACS, HER, etc.), wherein the system can output a radiology report with minimal or no input from a radiologist.

However, the system can be otherwise configured.

5. Method

Figure 11:
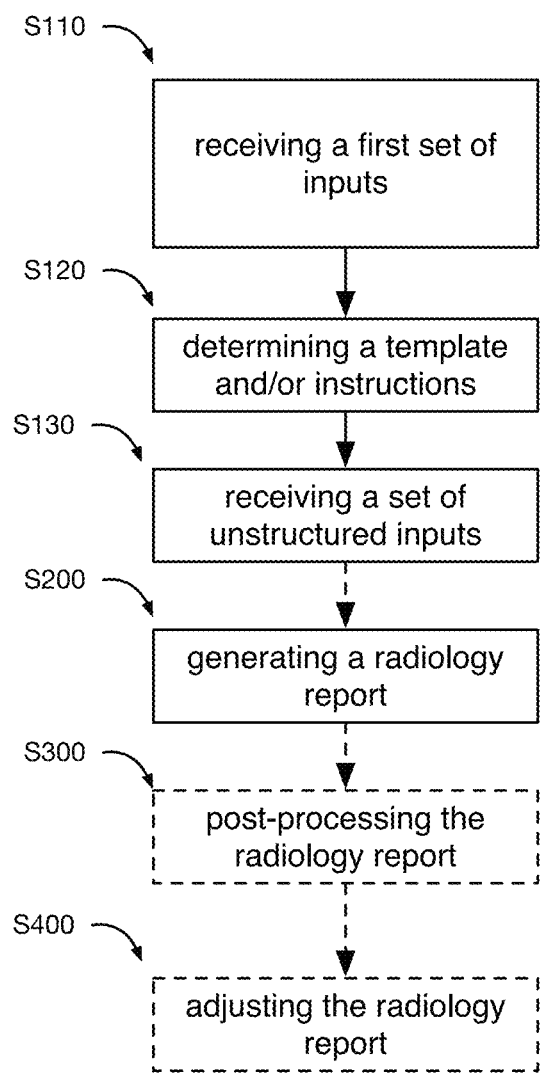
FIG. 11 is a schematic representation of a variant of the method.

As shown in FIG. 1, the method can include: determining a set of inputs S100 and generating a radiology report S200. The method can optionally include post-processing the radiology report S300, adjusting the radiology report S400, and/or any other suitable steps. In a first set of variants, (e.g., as shown in FIG. 11), determining a set of inputs can include: receiving a first set of inputs S110, determining a template S120, and receiving a set of unstructured inputs S130. In a second set of variants, additional or alternative to the first, the method can include performing fully automated reporting, which can include determining a first set of inputs that do not include manually input radiologist inputs (e.g., a dictated and/or typed finding), and generating a radiology report (e.g., a first draft) solely based on the first set of inputs. Optionally, further corrections and/or subsequent report drafts can be determined based on manually input radiologist inputs and/or any other suitable input.

All or portions of the method can be performed by one or more components of the system, using a computing system, using a database (e.g., a system database, a third-party database, etc.), by a user, and/or by any other suitable system.

All or portions of the method can be integrated within a standard radiology workflow, be configured to replace one or more processes in a standard radiology workflow, be performed independently of a standard radiology workflow, and/or be otherwise performed. All or portions of the method can be performed in real time (e.g., responsive to a request), iteratively, concurrently (e.g., in parallel), asynchronously, periodically, and/or at any other suitable time. All or portions of the method can be performed automatically, manually, semi-automatically, and/or otherwise performed.

While many of the examples described herein refer to generating and adjusting a radiology report, it should be understood that the system and method can be adapted to generate and adjust any other document, medical or otherwise, which can include: visit summaries and/or notes (e.g., notes in a patient's chart), operative reports, medical history (e.g., detailing past illnesses, surgeries, medications, allergies, family medical history, etc.), physical examination notes, progress notes (e.g., symptoms, treatment responses, plans for further care, etc.), diagnostic reports (e.g., test results, pathology reports from tissue samples, laboratory exam results, radiology reports, etc.) and/or interpretations, treatment plans (e.g., outlining prescribed medications, referrals, recommended surgeries, therapy plans, lifestyle changes, etc.), consent forms, discharge summaries (e.g., for hospital discharges, containing admission reasons, treatments, prescribed medications upon discharge, follow-up instructions, further care recommendations, etc.), treatment summaries, and/or any other suitable document.

5.1 Determining a Set of Inputs S100

Determining a set of inputs S100 can function to determine information associated with a patient, a study, a radiologist, and/or any other information that can be used to generate the radiology report. S100 can be performed: after an imaging study has been completed, before a radiologist has begun the reporting process, after the radiologist has begun the reporting process (e.g., after findings and/or other inputs have been provided by the radiologist), multiple times during the reporting process (e.g., before and after template determination, template generation, etc.), at any other time within a radiologist's reporting workflow, and/or at any other time.

Figure 2:
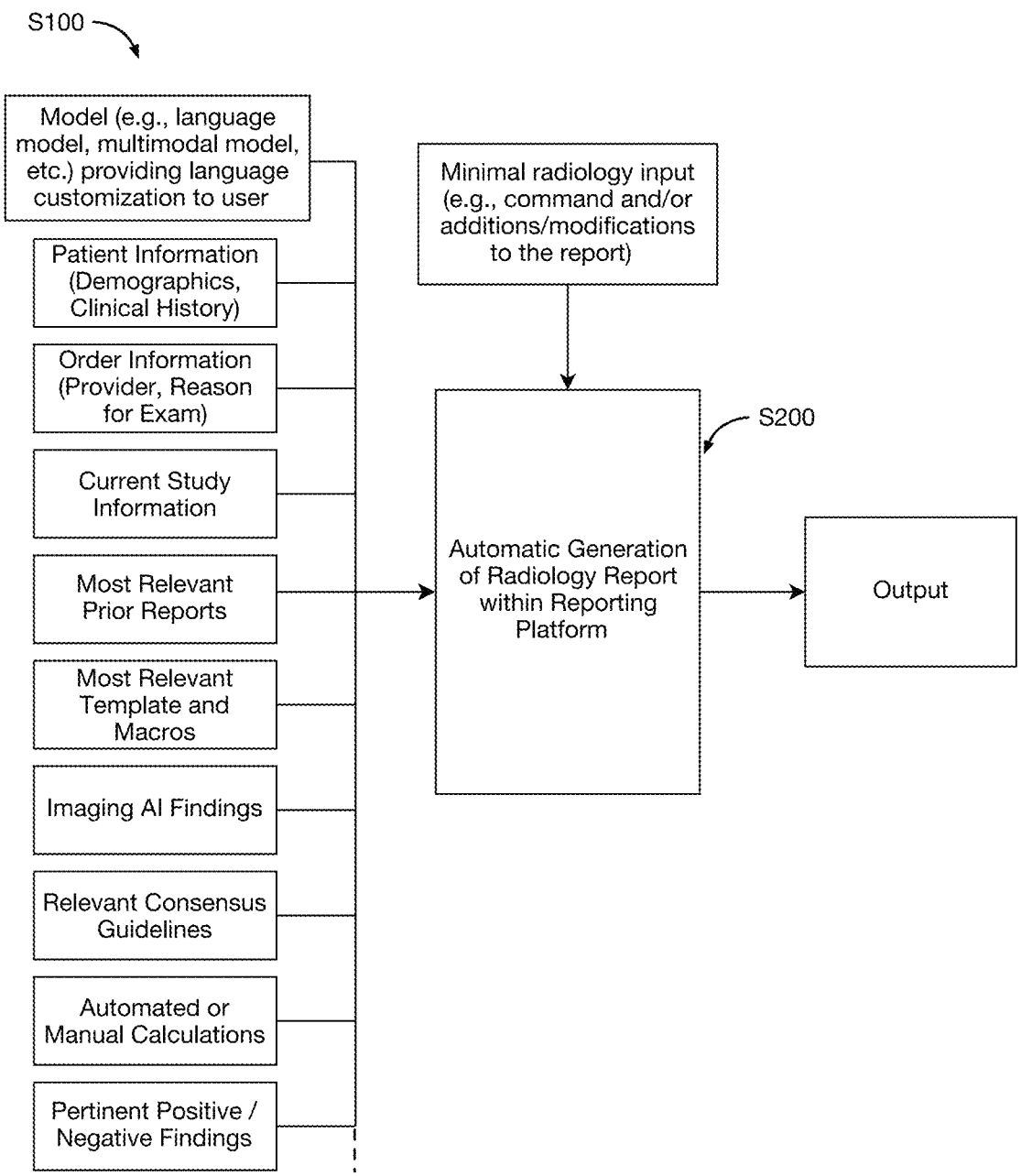
FIG. 2 depicts an example of generating a radiology report based on a set of inputs.

The set of inputs 40 can include, for the current study and/or a prior study: any information contained within and/or associated with the study, including: radiology reports and/or any subset of a radiology report (e.g., prior reports 45); study information (e.g., study imaging modality/technique, study type, study anatomy, study date, contrast usage, radiation dose information, associated radiology report, associated images, etc.); order information (e.g., provider, clinical indications/reasons for the study, healthcare facility, etc.); a set of preferences; patient information (e.g., demographics; clinical history and/or other patient history; information from a database; laboratory, surgical, and/or pathology results (e.g., ECG, EKG, blood test results, etc.); vitals; physician notes; medications; allergies; status; insurance coverage information; etc.); guidelines and/or procedures (e.g., consensus guidelines, insurance guidelines, billing guidelines, etc.); radiologist information (e.g., radiologist identifier); radiology group information; healthcare facility information; radiology standards; information from a database, storage, server, and/or software tools (e.g., EMR database, EHR database, RIS, CIS, PACS, etc.); ontologies; a set of images (e.g., x-ray, MRI, CT scan, ultrasound, PET scan, fluoroscopy, nuclear imaging, etc.); video; findings and/or associated information (e.g., finding characteristics, finding classifications, analyses, etc.); recommendations; diagnoses; calculations; templates and/or macros; one or more models (e.g., a language model associated with the radiologist); insights (e.g., derived from radiology reports, patient information, and/or other inputs); measurements (e.g., finding characteristics, clinically relevant measures such as BMI, etc.); any combination thereof; and/or any other information from any suitable sources. An example is shown in FIG. 2.

In examples, findings 50 can include: irregularities, anatomical features (e.g., nodules, masses, lesions, aneurysms, etc.), disease states, medical indications, and/or other suitable features of a radiology image. In examples, finding characteristics can include measurements (e.g., size, diameter, area, volume, extent, etc.), material composition, shape, location, quantity, and/or any other characteristics of a finding. Finding characteristics can additionally or alternatively include a comparison between a first finding characteristic and a second finding characteristic (e.g., across two sets of radiology images). Finding characteristics can additionally or alternatively include an aggregate (e.g., mean, maximum, etc.) of finding characteristics. In examples, finding classifications can include scores; incidental versus non-incidental; abnormal versus normal; positive versus negative; significant versus insignificant; pertinent versus not pertinent; and/or any other classification. In a specific example, pertinent positive and/or pertinent negative findings can be used as inputs.

In a first set of variants, an input can be received. In examples, the input can be received from: a database, storage, server, and/or software tools (e.g., the system, EMR database, EHR database, RIS, CIS, PACS, etc.); a radiologist and/or any other user (e.g., dictated, typed, macro-based entry, etc.); and/or received from any other source. In an example, the input can include information (e.g., patient information, study information, etc.) retrieved from a database. In another example, the input can include findings and/or associated information input (e.g., by a radiologist) via a user interface (e.g., the system user interface, a third-party user interface; etc.). In a first specific example, findings are the only inputs that are received from the radiologist (e.g., manually input by the radiologist) prior to initial report generation. In a second specific example, no inputs are received from the radiologist prior to initial report generation.

Receiving an input can include receiving a first set of inputs S110, which can function to receive information associated with a patient, a study, a radiologist, and/or any other information that can be used to determine (e.g., select, refine, create, etc.) a template, and/or used to generate the radiology report (e.g., to automatically fill in fields of the template). Preferably, the first set of inputs includes a set of medical information associated with a patient. The set of medical information preferably includes, for the current study, all or a subset of the information contained within and/or associated with the study. The set of medical information can additionally or alternatively include all or a subset of the information contained within and/or associated with a prior study of the patient, and/or any other suitable information (e.g., non-medical information).

Receiving an input can include receiving a set of unstructured inputs S130, which can function to receive a set of inputs (e.g., audio, text, etc.) in an unstructured form (e.g., in free-text, paragraph form, as a stream of audio, etc.). Preferably, S130 occurs after S110 and S120, but can additionally or alternatively occur after S110 and before S120, after an initial report is generated (e.g., during S300), and/or at any other suitable time. Preferably, the set of unstructured inputs includes a set of findings (e.g., radiology findings), but can additionally or alternatively include: questions, commands, corrections to a generated report (e.g., instructions to fix a value within the generated report), feedback (e.g., satisfaction with generated report, additional text to add to the generated report, etc.), and/or any other suitable input. The set of unstructured inputs can be received in the input interface as audio input (e.g., dictated by a radiologist into a dictation software), text input (e.g., typed by the radiologist into a text box), and/or any other form of input. The input interface can be configured to receive unstructured text and/or audio from a user within the reporting platform (e.g., side-by-side with the reporting platform). In a specific example shown in FIG. 12), the input interface can include a text box 144 to receive text (e.g., structured and/or unstructured).

However, inputs can be otherwise received.

Figure 3:
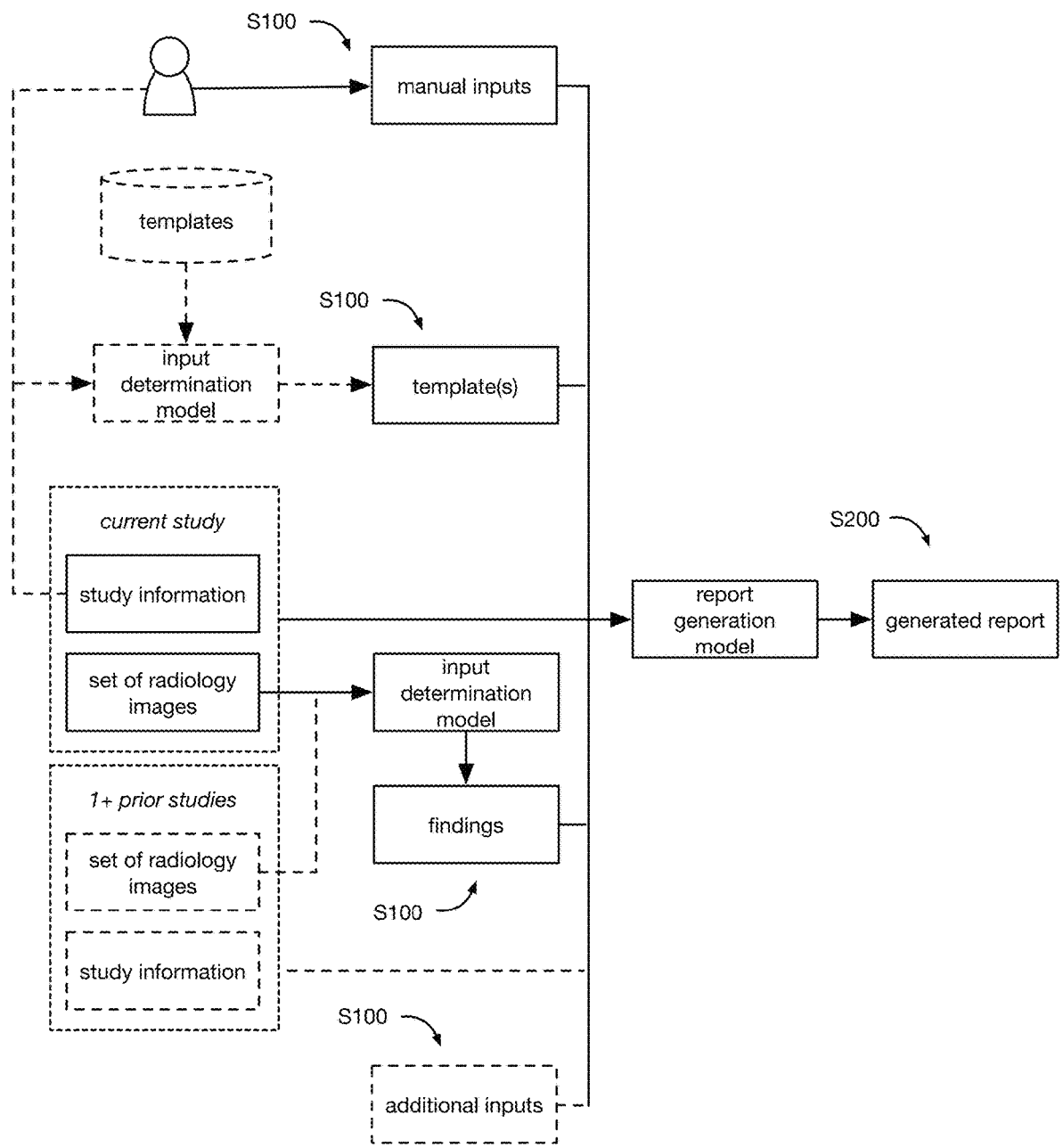
FIG. 3 depicts an example of determining inputs.

In a second set of variants, additional or alternative to the first set of variants, an input can be determined based on one or more other inputs. For example, the input can be determined using an input determination model. An example is shown in FIG. 3. Optionally, additional information (e.g., prior medical history, imaging studies, findings, study type, a field of the report, etc.) associated with the patient, billing, and/or other aspect of the report that is required to complete the report can be: requested (e.g., wherein a prompt for more information is provided to the radiologist at a radiology interface), retrieved (e.g., from a service such as PACS, RIS, EHR database, etc.) automatically and/or with permission (e.g., from the radiologist), predicted (e.g., using a model), and/or otherwise determined.

In a first embodiment, the input determination model can output findings and/or associated information (e.g., finding characteristics, finding classifications, etc.) based on one or more sets of radiology images (e.g., for the current study and/or for a prior study), patient history, consensus guidelines, manually inputted findings, and/or other inputs.

Figure 6A:
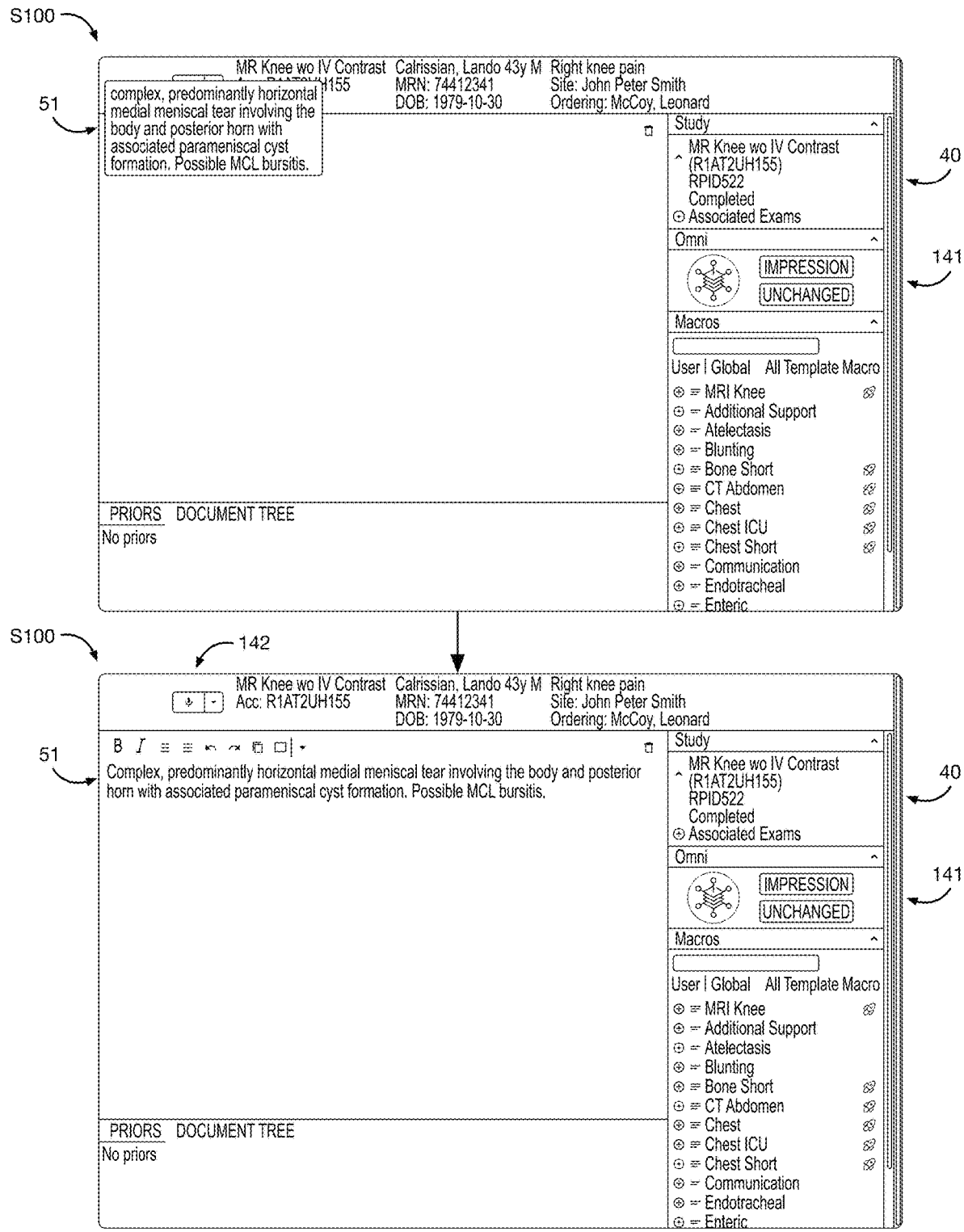
FIG. 6A depicts an illustrative example of determining findings based on dictated findings.

In a first example, findings (e.g., pertinent positive and/or negative findings) can be determined based on unstructured inputs (e.g., unstructured findings), including, for example, dictated or otherwise manually inputted (e.g., typed into the input interface) findings. In a specific example, the input determination model can select a subset of the unstructured inputs (e.g., dictated findings 51), structure the unstructured inputs, supplement the unstructured inputs (e.g., with findings determined based on images) and/or otherwise determine pertinent findings. An example is shown in FIG. 6A. Optionally S100 can include performing a speech to text operation (e.g., audio transcription) if the unstructured inputs include audio (e.g., radiologist dictation).

In a second example, findings and/or finding characteristics (e.g., measurements) can be determined based on the one or more sets of radiology images. In a specific example, the input determination model can output a disease trend (e.g., a list of findings that may be relevant to the current report and their reported characteristics on specific dates; optionally with the ability to map each specific finding automatically or manually across multiple prior reports) and/or other analyses (e.g., comparisons between prior radiology reports and the current radiology report) based on one or more prior radiology reports for the patient. In a second specific example, the input determination model can output a set of findings based on a current set of radiology images. In examples, the input determination model can include a set of trained models (e.g., deep learning models, computer vision models, neural networks, etc.) that automatically output the set of findings based on a set of inputs (e.g., image-based inputs, text-based inputs, etc.). In a third specific example, the system can include and/or interface with a third party image analysis software (e.g., an image AI vendor) that outputs findings based on the patient's radiology images. Optionally the input determination model can be used to reformat the findings received from the third party software (e.g., to fit the template, to match a desired reporting style, etc.).

In a third example, the input determination model can select multimedia items such as: mathematical calculation fields 43 (e.g., formulas, equations, charts, tables, graphs, etc.), images, links (e.g., to key image(s) on PACS and/or another image platform, to a medical database, to a piece of data within a patient's historical records, etc.), and/or functionality (e.g., relevant to: a finding and/or associated information, the current study, the patient, any other input, etc.), wherein the selected multimedia items can be inserted into the radiology report (e.g., within templates and/or macros). In examples, importing multimedia items to create a multimedia report (e.g., including text and at least one of: mathematical calculation fields, images, links, and/or any other multimedia item) can adhere to a published standard (e.g., THE standard, IMR standard, etc.). In a specific example, the calculation fields can be manually populated and/or automatically populated (e.g., based on measurements determined based on radiology images) to calculate a finding characteristic (e.g., volume); an example is shown in FIG. 8. In a specific example, the input determination model can retrieve a relevant mathematical formula (e.g., ellipsoid volume formula) based on an input (e.g., a finding of a tumor) received. Optionally, the formula can be presented at the user interface with an input component (e.g., text boxes spaces within the formula for missing data fields such, empty variables below the formula, the input interface, etc.), wherein the radiologist can provide further structured and/or unstructured input (e.g., defining a variable within the formula). The output of the formula 44 (e.g., tumor size) can be automatically calculated based on the further input. A mathematical calculation field 43 can optionally include a visual representation of data, such as a chart (e.g., line chart, bar chart, scatter plot, survival curve, flow chart, box plot, funnel plot, forest plot, Sankey diagram, etc.), table (e.g., patient data table, clinical trial results table, treatment comparison table, adverse events table, laboratory values table, drug dosage table, patient demographics table, surgical outcomes table, etc.), and/or any other visual data structure. In a specific example shown in FIG. 13, the findings section can be populated with a chart/table, which can optionally be further used to generate other findings, impressions, and/or any other section of the report. In examples, inserting multimedia items and/or findings into a report can be performed: automatically (e.g., received directly from PACS), in response to a user input (e.g., click, hotkey, button, etc.), In a fourth example, finding classifications and/or recommendations can be determined based on findings (e.g., findings automatically determined using a first input determination model, findings manually input by a radiologist, etc.) and consensus guidelines, using the input determination model (e.g., a second input determination model). In a specific example, the input determination model can be used to determine when a specific finding no longer needs additional follow-up based on national consensus guidelines or best practice recommendations, given that the follow-up has already been performed and their associated exam dates.

In a fifth example, findings and/or analyses (e.g., known, suspected, and/or possible diagnoses for the patient) from prior radiology reports can be determined using the input determination model based on prior radiology reports, order information, patient information, and/or any other inputs. In a specific example, the findings and/or analyses can be manually or automatically associated with findings in the current report. In examples, determining findings, associated information, and/or any other inputs can use systems and/or methods as described in U.S. application Ser. No. 18/202,582, filed 26 May 2023, which is incorporated in its entirety by this reference.

The findings and/or associated information can optionally be: inserted (e.g., automatically and/or triggered by a user action; optionally with modification from a radiologist) into the radiology report, used as an input (e.g., to a report generation model, to another input determination model, etc.), displayed to a radiologist (e.g., as a reminder notification, as text that can be inserted, as analysis on what the radiologist should discuss in the report, etc.), embedded directly within personal or system templates and/or macros (e.g., in a reporting platform), inserted with or as part of a specific report type (e.g., with results of calculations automatically included in the correct location in the report), trigger a downstream action (e.g., automatically, based on a manual user input, etc.), and/or be otherwise used. In examples, downstream actions can include: notifications and/or other communications (e.g., to another provider, caretaker, emergency contact, establishment of a communication between two or more parties, etc.), referrals (e.g., to a relevant specialist, to a relevant clinical trial, etc.), follow-up care coordination (e.g., for one or more actionable findings), streamlined (e.g., automated) coding (e.g., for billing purposes), a critical results workflow, and/or any other suitable action. In examples, the method can include a critical results workflow, wherein a certain list of critical results (e.g., findings, macros, templates, etc.), which may vary by health system, radiology practice, and/or any other identifier, can automatically trigger immediate downstream actions (e.g., notifications within the EHR, notifications outside the EHR to an ordering and/or referring provider, etc.). In a specific example, the addition of a specific critical result (e.g., the selection of a template, the determination of a finding, the selection of a macro, etc.) associated with a certain critical condition (e.g., a pulmonary nodule) may trigger (e.g., automatically) one or more downstream actions including (e.g., communications with and/or referrals to a Pulmonary clinic and/or a thoracic surgeon).

Figure 12:
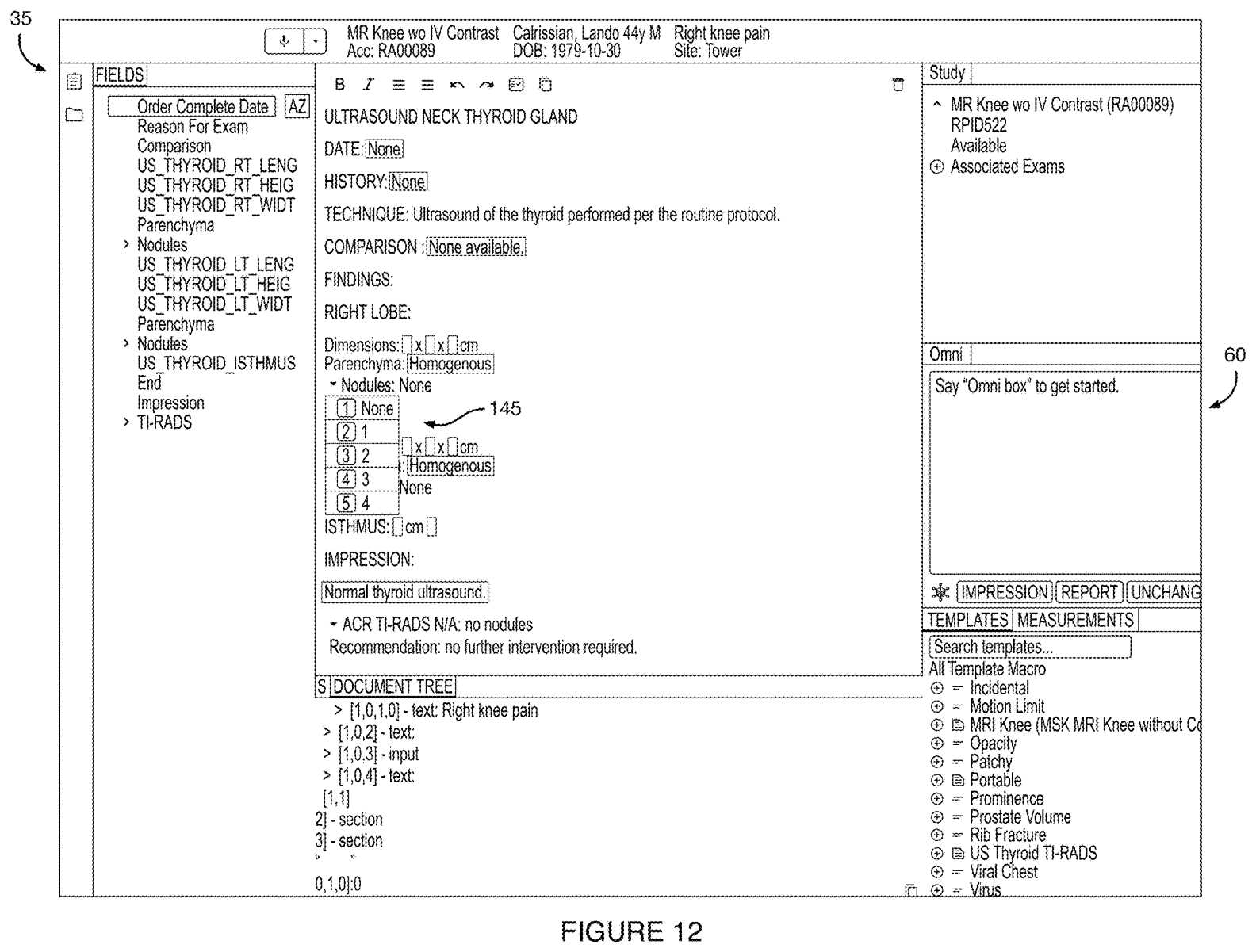

Optionally, after a first set of findings are determined (e.g., based on unstructured input from the radiologist, based on a set of patient images, etc.), the input determination model can determine a set of fields (e.g., a second set of findings, finding characteristics, a formula, etc.) that depend on the first set of findings, and optionally automatically insert the fields into the report, which can serve the benefit of flagging areas where additional information is needed to the radiologist to ensure full completion of the radiology report. In an example, if the system receives a set of input (e.g., dictation from the radiologist) indicating a nodule is present within a radiology image, the input determination model can determine a set of fields (e.g., size, margins, composition, etc.) to insert into the radiology report along with the finding of nodule present. Optionally, the input determination model can determine a set of nested fields that depend on the first set of fields, and so forth. The system can present the radiologist with one or more means to complete the field, including a text box (e.g., adjacent to the field), a pick list (e.g., clear margins, close margins, and involved margins; etc.) and/or dropdown menu 145 (e.g., as shown in FIG. 12), the input interface, and/or any other suitable means. Optionally, the radiologist can modify the field directly from the input interface (e.g., wherein the input interface is not directly proximal the field) by typing, dictating, and/or otherwise providing input, without needing to manually modify the field (e.g., by clicking or typing proximal to the field). In a specific example, the radiologist can input the dependent fields after inputting the finding, and the input determination model will automatically insert the dependent fields in a proper location within the section containing the finding.

In a second embodiment, the input determination model can determine a template and/or macro (e.g., as expanded in S120). Optionally, the template and/or macros may contain a set of dependent fields and/or nested fields. In examples, templates and macros may contain one or multiple display means for users to complete the dependent field (e.g., pick lists, dropdown menus, text box, etc.). Optionally, templates, macros, pick lists (or any similar means of presenting a predefined list of selections such as a dropdown menu, etc.), and/or any other suitable components can be nested within other templates, macros, pick lists, and/or any other suitable components. Optionally, the system can include multiple levels of nesting.

In a third embodiment, the input determination model can output one or more selected prior studies and/or associated information (e.g., radiology report, images, etc.) based on, for the current study and/or the prior studies: study information, radiology report information (e.g., specific language present in radiology reports for the prior studies), order information, patient information, radiologist information, and/or other inputs. The selected prior studies and/or associated information can be selected to be relevant to: the current study, the patient, the radiologist, a combination thereof, and/or any other inputs. In an example, the prior studies and/or associated information can be selected from a database (e.g., a database of prior studies specific to the patient). In an illustrative example, the input determination model can be trained (e.g., training a machine learning model; determining a classification, similarity, and/or ranking model; etc.) to select one or more prior studies and/or associated information with similar study information relative to the current study. The selected prior studies and/or associated information can optionally be: used as an input (e.g., to another input determination model, to a report generation model, etc.), displayed to a user, stored, and/or otherwise used. The selected prior studies and/or associated information (e.g., radiology reports) can optionally be summarized (e.g., using a machine learning model or other model) into a summary that contains relevant information, wherein the summary can be displayed to a user and/or be otherwise used.

Inputs can be determined and/or used in any order. In an illustrative example, relevant template(s) can be selected prior to receiving manual inputs (e.g., dictated findings) from a radiologist. In another illustrative example, negative findings can be auto-filled into the template prior to receiving manual inputs, and positive findings can be determined and inserted into the template after manual inputs (e.g., dictated findings) are received from the radiologist. Optionally, pertinent negative findings can be determined based on one or more positive findings, wherein pertinent negative findings do not need to be mentioned except when an associated positive finding exists. In an example, if a positive finding (e.g., "diffuse inflammation about the body and tail of the pancreas, with trace fluid") is inserted, any relevant pertinent negative language (e.g., "no definite evidence of abscess or necrosis") can be determined and inserted.

One or more inputs can optionally be determined using the report generation model (e.g., a multimodal model). For example, S100 can be performed during S200. In a specific example, the report generation model outputs and/or modifies radiology report text using a combination of language model(s) and additional machine learning model(s). In this example, the report generation model can: generate inputs (e.g., findings) based on radiology images and/or other inputs; incorporate comparisons between the current study and prior studies (e.g., incorporating the concept of time); and/or otherwise incorporate multiple modes of data in generating and/or modifying radiology report text.

However, the set of inputs can be otherwise determined.

5.2 Determining a Template S120

Determining a template S120 can function to identify a template from which the radiology report can be generated. Additionally or alternatively, S200 can function to identify a set of one or more instructions (e.g., macros), to identify a template for any other medical document, and/or otherwise function. The templates can be retrieved from a database which can optionally include templates created and saved by the radiologist, generated (e.g., based on a historical set of radiology report created by the radiologist), and/or otherwise determined. In examples, the input determination model (e.g., a template determination model, a macro determination model, etc.) can determine a template and/or macro based on any of the inputs received at S100.

Preferably, determining a template S120 (e.g., with the input determination model) is performed based on the set of inputs received at S100, which can include: study information, radiology report information, order information, patient information, radiologist information, radiology group information, healthcare facility information, the presence or absence of prior studies, the findings, the patient identifier, the treatment, and/or other inputs. Determining the template can additionally or alternatively be performed based on the set of unstructured inputs received at S130, and/or any other suitable information.

S120 can include determining a set of fields 35 within the template. In examples, the set of fields can include: report sections (e.g., section headers), patient information fields, study information fields, findings fields, comparison fields, fields associated with any of the set of inputs, and/or any other suitable fields. Determining the set of fields can include: retrieving the template with a set of fields already include in the template, optionally adding one or more additional fields to the set of fields, optionally removing one or more fields from the set of fields, determining all fields of the template, and/or otherwise determining the set of fields. Optionally, the set of fields can be displayed to the user: within the radiology report, adjacent to the radiology report (e.g., as shown in FIG. 12), and/or otherwise displayed. Optionally, field dependencies can be displayed as a set of dropdown list/expandable list (e.g., as shown in FIG. 12).

The input determination model can output one or more selected or ranked templates and/or instructions (e.g., rules, mappings, macros, etc.) based on the set of inputs received. For the sake of simplicity, the instructions will be equivalently referred to herein as "macros," but can take any other suitable form. In variants, S120 can optionally include determining a single template, or determining a set of templates, wherein the radiologist can optionally select a template and/or macro from a presented set (e.g., a ranked list; in a drop-down sort list; unsorted; etc.) of the selected or ranked templates and/or macros. The templates and/or macros can optionally be selected/ranked to be relevant to: the current study, the radiologist, the radiology group, the healthcare facility, the patient, a parameter specified by the radiologist (e.g., in a drop-down menu), and/or any other input. In an example, templates and/or macros (e.g., a subset of templates and/or macros) can be selected from a database of templates and/or macros (e.g., a database specific to the radiologist, radiology group, and/or healthcare facility). Optionally, macros can additionally or alternatively be determined based on the selected template (e.g., wherein a template is associated with/stored with a set of macros).

In a set of specific examples, one or more macros is selected in S120 (e.g., with a template, in absence of a template, etc.), where a macro prescribes a set of commands (e.g., rules, mappings of inputs to outputs, formulas, etc.) that are implemented in an automated fashion.

The selected templates and/or macros can optionally: be inserted (e.g., automatically and/or triggered by a user action) into the radiology report, be used as an input (e.g., to a report generation model), replace a template and/or macro currently in the radiology report (e.g., switch between templates, automatically transferring information from one template to another), and/or be otherwise used.

S120 can include determining a set of macros based on: the template (e.g., wherein a template includes an associated set of macros), the radiologist (e.g., wherein the radiologist has macros that they have: defined, historically used frequently, historically used frequently in combination with the other inputs determined, etc.) and/or radiology group, any of the set of inputs (e.g., imaging modality, order type, pathology, etc.) determined at S100 (e.g., wherein a set of radiologists have macros that they have historically used more frequently in combination with a subset of the specific inputs), and/or otherwise determined. Optionally, an initial set of macros can be determined based on a first set of inputs, and a set of one or more additional macros can be determined after a second set of inputs (e.g., findings, unstructured findings, etc.) are determined. S120 can optionally include determining a set of multiple macros, and sorting the macros (e.g., determining a priority for each macro), wherein all or a subset (e.g., a top set of one or more) of the sorted macros are presented to the user and/or automatically inserted into the template. In variants, sorting macros can be based on a relevancy score, determined based on: the template, the inputs (e.g., information within the study, dictated content within the report, etc.), and/or any other suitable information.

Determining a template S120 can be performed using an input determination model, rule-based methods, by receiving a selection from a user, and/or otherwise performed.

In a first variant, determining the template and/or macro can include receiving a template and/or macro selection from the radiologist. Optionally, the selection can be used as a training target to update the input determination model (e.g., to update a radiologist-specific input determination model).

In a second variant, S120 can include using rule-based methods to determine the set of templates and/or macros. Rules can indicate a subset of templates and/or macros to consider/not consider for selection based on one or more inputs of the set of inputs. In a specific example, the template must match the imaging modality included in the study information. Optionally, the radiologist can specify and store their own rule preferences for template retrieval. In examples, rules can be used as inputs to the input determination model (e.g., a rule-based input determination model), to limit a search space of the input determination model, to filter model outputs, and/or otherwise applied. Additionally or alternatively, S120 can utilize purely rule-based methods to determine a template and/or macro, or purely non-rule-based methods. Rules can be: learned (e.g., by an input determination model that updates over time based on the templates and/or macros selected by the radiologist), manually specified by a radiologist (e.g., "if this procedure type, then pull this template"), and/or otherwise determined.

In examples, rules can specify that the template should match a set of values included in the inputs, for example: an imaging modality (e.g., CT), a procedural type (e.g., x-ray), a body part (e.g., chest), a patient demographic (e.g., pediatric, gender, age, etc.), a clinical indication (e.g., suspected fracture), study information, a radiologist group, a report complexity (e.g., as determined based on a complexity parameter associated with the inputs), abnormal findings (e.g., wherein templates including sections for the particular abnormal findings are retrieved), follow-up recommendations (e.g., wherein templates including sections for follow-up recommendations are retrieved), ordering and/or referring provider, ordering and/or referring provider practice, a location where the study was performed (e.g., a specific site; a site classification such as ER, inpatient, ICU, CCU, outpatient, etc.; etc.), and/or any other suitable input.

In examples, rules can be applied hierarchically, wherein each rule can have an associated importance value (e.g., weight). Rules with a greater importance value can be prioritized in the search for a template/macro selection over rules. The rule hierarchy can be learned (e.g., by an input determination model that learns hierarchical preferences of the radiologist based on historical preferences), prescribed by a user (e.g., the radiologist), rule-based (e.g., wherein certain rule types take precedence over other rule types), and/or otherwise determined.

In a third variant, determining the template and/or macro can include using LLM-based methods. In a specific example, the input determination model can use a prompt-based approach. In an illustrative example, the input determination model can combine a large language model (LLM) with an information retrieval system (e.g., a semantic search engine), wherein the task of the LLM (and prompt) can be to generate the best possible template search string. In a specific example, the prompt instructs the LLM to generate a template search string, which is then used with an information retrieval system to select one or more templates and/or macros. In a second specific example, the input determination model can use an LLM in combination with rule-based constraints to generate a radiology template.

In a fourth variant, determining the template and/or macro can include using learning-based methods (e.g., machine learning). The input determination model can be trained to select one or more candidate templates and/or macros based on historical selections and/or radiology reports generated by the radiologist. Optionally, learning-based methods can be combined with any of the other variants (e.g., wherein rules are learned over time, wherein the outputs of an LLM are learned over time based on a particular radiologist's style, wherein the most likely template for a particular radiologist to select is learned over time, etc.). Selections of the radiologist (e.g., of a template and/or macro), edits to a template and/or macro, responses (e.g., of a physician to the radiology report, flagged errors after completion, etc.), detected errors (e.g., by an error detection module), and/or any other suitable outcomes can be used as a training target to retrain the input determination model.

Optionally, S120 can include a fallback procedure, which can include performing an initial search among a database of templates and/or macros using a first search method (e.g., using rule-based methods, using a prompt-based approach, etc.). If an insufficient quantity (e.g., based on a predetermined number) of matches are found (e.g., if no existing templates have rules that match/can be mapped to using the set of inputs), the fallback procedure can include performing a secondary search among the database using a second search method (e.g., machine-learning based approaches) and/or generating a new template (e.g., based on an existing template).

In examples, the input determination model can be trained based on historical template and/or macros preferences for a radiologist (e.g., each associated with a study type, patient information, and/or any other inputs). In an illustrative example, the input determination model can be trained (e.g., training a machine learning model; determining a classification, similarity, and/or ranking model; etc.) to select one or more templates and/or macros to match the templates and/or macros historically used by the radiologist for the current study type.

Additionally or alternatively, S120 can include determining updates (e.g., improvements) to templates and/or macros (e.g., using the input determination model). In a first variant, updates are determined based on edits (e.g., frequent edits, a single edit, etc.) made to templates and/or macros by the radiologist. In a second variant, updates are determined based on the first set of inputs received at S110. For example, S120 can include selecting a best fit template and/or macro and refining (e.g., inserting additional fields into the template based on a patient's medical history) the best fit template and/or macro (e.g., using a report generation model) based on the first set of inputs received at S110. In a third variant, updates are determined based on an input from the radiologist (e.g., the unstructured input received at S130). The updated templates and/or macros can be: output as the selected templates and/or macros, stored/saved (e.g., as an updated personal template and/or macro), updated within the selected templates and/or macros (e.g., with an indicator displaying the updates), and/or otherwise used. However, determining updates to templates and/or macros can be otherwise performed.

Optionally, S120 can include automatically filling in one or more fields of the template (e.g., based on a first set of inputs used to determine the template and/or a second set of inputs). Preferably, S120 includes automatically filling in patient information, billing information, study information, order information, radiologist information, and/or any other suitable information. However, any information can be presented to the radiologist for verification, not automatically filled, adjusted after an error correction step, and/or otherwise used. Additionally or alternatively, the system can default to filling in any findings fields of the template without associated information with a negative finding. Optionally, as further inputs are received (e.g., unstructured inputs, dictated findings, checkbox selections, etc.), the input determination model can replace the negative finding with a positive finding determined based on the further inputs.

S120 can optionally include managing a set of templates within a database and/or network containing a plurality (e.g., hundreds, thousands, hundreds of thousands, millions, billions, etc.) of templates. The invention can provide a more robust system for managing templates, as compared to conventional systems and methods, by managing stored templates with a versioning file system (e.g., pointer-based file system, distributed version control system, snapshotting file system, tree-based file system, etc.), which can optionally be hosted on a web-based hosting service (e.g., cloud), on a local device, and/or otherwise located. In variants, templates within the version control system can be modified, added, deleted, moved, reverted, merged, forked, and tracked across different versions and branches. Optionally, the version control system can include user-specific local files (e.g., templates), wherein the folder structure can include directories for a shared repository alongside separate directories for each user's local working copy, allowing for individualized changes and version tracking.

In variants, templates can be stored with dependencies on another parent template, on a set of preferences, on a set of inputs to the template (e.g., a patient, a study modality, a pathology, etc.), and/or another suitable dependency. In examples, the set of preferences can be stored in association with an individual (e.g., a radiologist, an ordering physician, a patient, etc.), a group (e.g., a radiology group, a hospital, a managed care consortium, an insurance provider, etc.), and/or any other suitable entity. In examples, an update (e.g., to a parent template, a patient's case information, and/or to a preference set, to a macro stored with the template, etc.) can be propagated to one or more (e.g., all) dependent templates: automatically, pending approval (e.g., permission) of a user (e.g., a radiologist, a radiology group, a medical group, an administrator, etc.), and/or otherwise propagated. Linking templates based on hierarchical dependencies and/or inputs to the templates can provide the benefit of reducing manual effort and time to modify a plurality of templates (e.g., if an error in a first template appear in several copies of that template, correcting the first template can automatically function to correct the copies as well).

Preferably, if a parent template is modified, all templates that depend on the parent template (e.g., all child templates) can be modified (e.g., automatically, if a user opts to push the modification to all children, etc.). Additionally or alternatively, if a user is editing a child template, the system can present an option for the user to propagate that edit up to the parent template (and optionally further down to other child templates of the parent template). Additionally or alternatively, only modifications that are relevant (e.g., appear within) both a modified template and a linked template (e.g., the parent template, the child template, etc.) are propagated to the linked template. In a specific example, a parent template for a particular study/imaging modality and/or pathology (e.g., cancer) can have child templates associated with different potential outcomes (e.g., clear margins vs. positive margins). A modification to a field associated with an outcome may not be propagated to the parent template, while a field associated with another value (e.g., study description) may be propagated to the parent template (and optionally to the child template(s) associated with the different potential outcomes). However, a template can be modified without propagating the edit to another template.

In variants, templates can be stored with dependencies on other templates based on information included within a radiology report (e.g., study type, imaging modality, pathology, etc.). If a user (e.g., radiologist) modifies a first template (e.g., a template open within an active radiology reporting session) associated with a first set of inputs (e.g., an imaging modality), the modification can optionally be propagated to a second set of templates (e.g., parent templates, child templates, unlinked templates, etc.) that are also associated with the first set of inputs (e.g., a modification to a template for a particular imaging modality can be propagated to other templates for the same imaging modality).

S120 can optionally include managing a set of macros. In a first variant, macros can be managed in the same way as explained above for managing a set of templates. In a second variant, macros can be stored in association with the templates (e.g., as inputs to the templates), wherein modifications to macros within a first template can optionally be propagated to a second template using the same macro.

However, the template and/or macro can be otherwise determined.

5.3 Generating a Radiology Report S200

Generating a radiology report S200 can function to generate all or a portion (e.g., most, greater than 50%, greater than 75%, etc.) of a radiology report based on the set of inputs. For example, the radiology report can be generated with minimal or no manual inputs from a radiologist. S200 can be performed after S100, in response to S100, automatically (e.g., zero-click, zero-typing), in response to a user action (e.g., minimal user action, single-click, single-command, etc.), and/or at any other time. In a specific example, a radiology report can be generated in response to a voice command (e.g., without clicks, without typing, etc.).

The radiology report (and/or the template from which the report is generated) can include a set of fields. In a preferred set of variants, the fields can include one or more inter-field dependencies (e.g., formula dependencies, data dependencies, etc.), which can provide the benefit of reducing a radiologist's workload by automatically inserting a value determined based on a first field (e.g., the value itself, an outcome of an equation that includes the value as a variable, etc.) into a second field so that the radiologist does not need to manually fill out each field. The report generation model can optionally pull a value from a first field into a second field, and/or compute the value of the second field based on the value in the first field. However, the fields can additionally or alternatively be independent. In a first example, if multiple fields within a report all refer to the same variable (e.g., a measurement, a finding, etc.), when one of the fields is filled in with a value, each of the other fields is automatically filled in with the value (e.g., the variable is set to equal the value). A specific example is shown in FIG. 13, wherein a value for a coronary calcium score is extracted from a first field within a chart, and copied into a second field in an impression section. Optionally, generating a report can include replicating a field into another section of a report (e.g., wherein each field points to the same value). In a second example, fields can have values that depend on the values contained within one or more other fields. In examples, determining the value of a field can include: performing a lookup function based on another field (e.g., if field A value=X, then field B value=Y), performing string interpolation on another field (e.g., directly inserting a value from field A into a text string that includes field B), calculating the output of an equation based on other fields, and/or any other suitable function.

Figure 10:
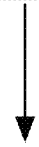
FIG. 10 depicts an illustrative example of generating an impression for a radiology report based on dictated findings.

The report generation model can output all or a portion of the radiology report (e.g., text for the radiology report) based on the set of inputs. The output can be structured (e.g., multiple sections of findings each specific to an anatomical structure), unstructured (e.g., in free-text, paragraph form), and/or otherwise configured. An example of a generated radiology report 30 is shown in FIG. 6B and FIG. 6C. An example of generating an impression section 60 of a radiology report based on the findings 50 is shown in FIG. 10.

Generating the radiology report S200 can optionally include determining a set of findings and inserting the set of findings into the template. The findings can be determined (e.g., as described in S100) based on the set of inputs received in S100 (e.g., the findings inputs received from the radiologist and/or a third party software).

Determining the set of findings can optionally include structuring the set of inputs received at S100. In examples, structuring the set of inputs can include referencing the inputs against a database of medical ontology to determine a finding and/or other data field to enter into the report. In examples, structuring the set of inputs can include determining a set of one or more codes (e.g., within a universal ontology/classification system such as a LOINC code, procedure codes, SNOMED, etc.) based on the set of inputs received in S100. The code can be: inserted directly into an appropriate field within the radiology report, provided as an input to a model (e.g., the report generation model, and LLM-based model, etc.), and/or otherwise used to generate the report. In examples, structuring the set of inputs can include determining a plurality of findings and/or other data values contained within a set of unstructured inputs received at S130. In examples, structuring the set of inputs can include determining an appropriate field for an input (e.g., finding, datum, etc.) within a report and/or report template. Optionally, structuring the set of inputs can enable users to search, filter, and/or otherwise specify and find a record associated with a specific diagnosis and/or set of findings within subsets of historical reports and/or patient populations.

Determining the set of findings can optionally include generating outputs (e.g., text, data, etc.) based on the set of inputs (e.g., unstructured inputs), which can include expanding the information contained within the inputs (e.g., determining a full form version of a shorthand for a finding entered by a radiologist, adding context for clarification, etc.), modifying the format (e.g., language, language style, data format, etc.) of the inputs, and/or otherwise generating outputs. In an example, determining a set of findings can include using a set of trained models (e.g., input determination models) to automatically generate a set of text to populate a plurality of fields of the report template. Optionally, the set of text is generated with a desired writing style, which can match a writing style of the radiologist (e.g., such as described in U.S. patent application Ser. No. 17/020,593, filed 14 Sep. 2020, which is incorporated herein in its entirety by this reference), a writing style of another specified radiologist (e.g., a particular attending, a particular specialist, etc.) and/or other medical professional, a writing style of another specified group (e.g., radiology group, insurance group, hospital group, etc.), a generic style, a style that conforms with one or more standards (e.g., quality metrics, professional organization standards, etc.), a writing style catered to a particular audience, and/or any other style. In optional variants, the system (e.g., radiology reporting platform) can store a plurality of writing style options, and offer users the option to select and/or otherwise specify a desired reporting style (e.g., via a multiple choice selection, via the input interface, etc.). In optional variants, the system can enable a user to specify a style for: the entire report, one or more individual sections of a report, no sections of a report (e.g., where a default style is implemented), and/or otherwise specify the style. In variants, a writing style can be catered to a particular audience (e.g., patients, medical professionals, insurance groups, etc.). In a specific example, a patient-friendly writing style can include language that can be interpreted by non-medical professionals, which can include: translations of technical medical terminology (e.g., inserted into the text, a link to a glossary of medical terminology, an ability to hover over a term to further define the term, etc.), links to patient resources associated with findings (e.g., for each specific finding), a less formal writing style, and/or any other suitable patient-friendly writing. In variants, generating outputs can confer the benefit of fully filling out the report using models (e.g., natural language processing models, LLM-based models, etc.), including expanding beyond just what was manually input by the radiologist, thereby saving the radiologist time and effort.

A report generation model can optionally include and/or interface with one or more input determination models, language models, and/or any other models arranged in sequence, in parallel, and/or with any other architecture. In a first variant, a set of inputs and optional prompts are provided to the report generation model (e.g., functioning as a single model), wherein the report generation model outputs all or a portion of the radiology report (e.g., a template, a findings section, an impression section, etc.). In a second variant, different sets of inputs (and optional prompts) are provided to different models within the report generation model. For example, a first set of inputs and optional prompts are provided to an input determination model to output one or more selected templates and/or macros; and a second set of inputs (including the selected templates and/or macros) and optional prompts are provided to a language model to output all or a portion of the radiology report.

In an example, generating the radiology report can include: using an input determination model (e.g., within the report generation model) to select relevant templates and/or macros (via S100) based on a first set of inputs, inserting the relevant templates and/or macros into the radiology report, updating one or more fields in the radiology report (e.g., in the templates) based on a second set of inputs (e.g., comparisons, finding and/or associated information, measurements, etc.; determined via S100), generating text (e.g., findings text, impression text, comparison text, etc.) using one or more language models based on a third set of inputs, and inserting the text at appropriate locations in the radiology report (e.g., within the templates and/or macros), and/or performing any other report generation processes. The sets of inputs can be the same, different, overlapping, non-overlapping, and/or otherwise configured. In a specific example, generating the radiology report can include updating (e.g., automatically updating) specific fields within the template, such as clinical indication, comparison, study technique, contrast usage, radiation dose information, recommendations, and/or any other fields associated with any input. In another specific example, the generated text can incorporate any pertinent negative and/or positive language that can be related and/or unrelated to findings manually input by the radiologist.

Inputs provided to the radiology report model can optionally be structured, which can function to increase security and/or to clarify instructions for the radiology report model. In examples, inputs from a radiologist can include a radiologist tag (e.g., <rad/> tags), prompts from a prompt engineer can include a prompt engineer tag, inputs automatically determined can include an input determination model tag, and/or inputs can be otherwise structured. Outputs from the model can include structured data, unstructured data (e.g., unstructured text), and/or any other output. In a specific example, structured data can be inserted (e.g., re-inserted) into a structured document (e.g., into a radiology report template) such as in the fields, sections, and/or any other location. One or more components of the structured document (e.g., specific pick lists and/or text) can optionally be retained.

Figure 4A:
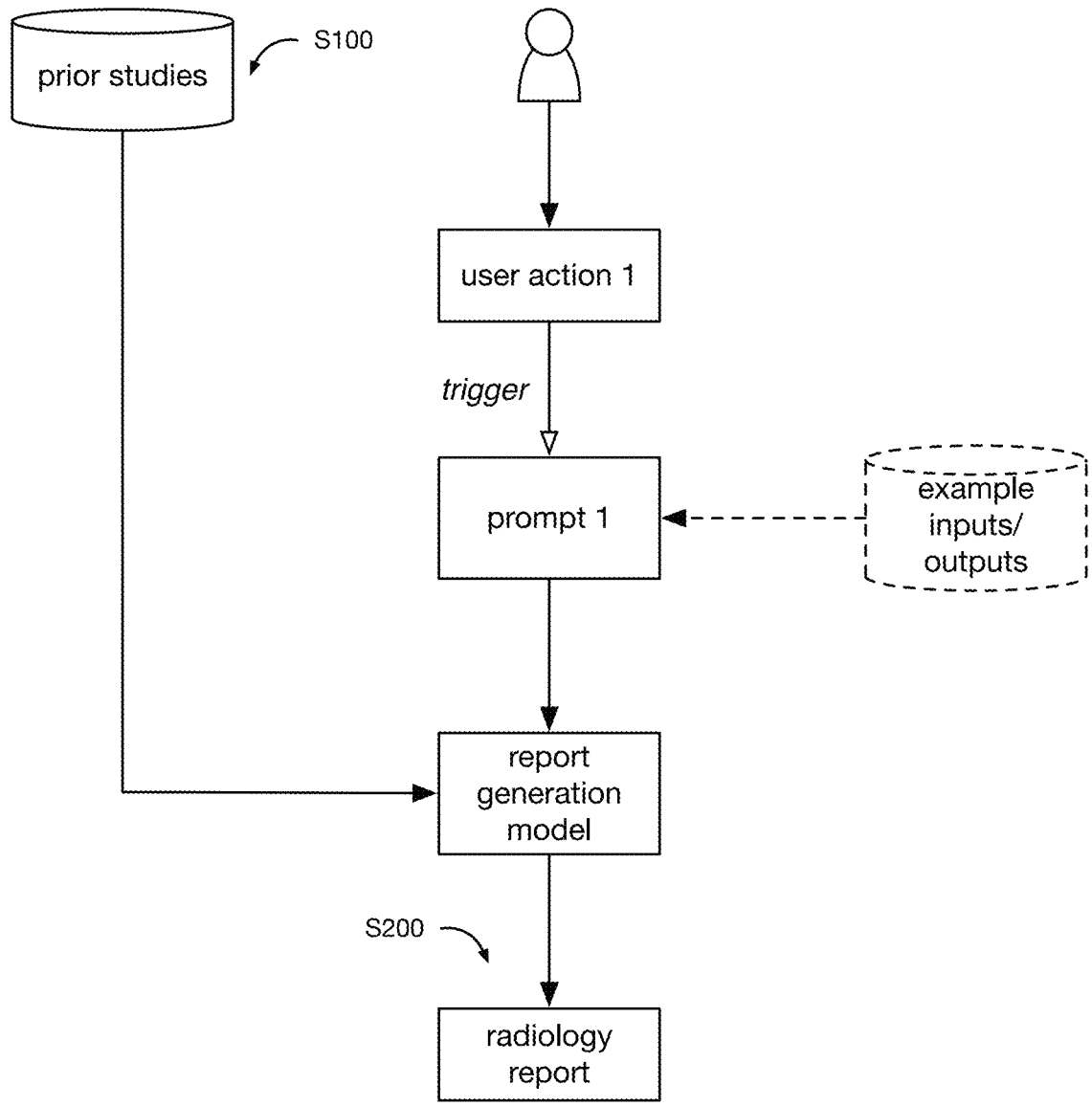
FIGS. 4A and 4B depict examples of determining report generation parameters based on a user action.
Figure 4B:
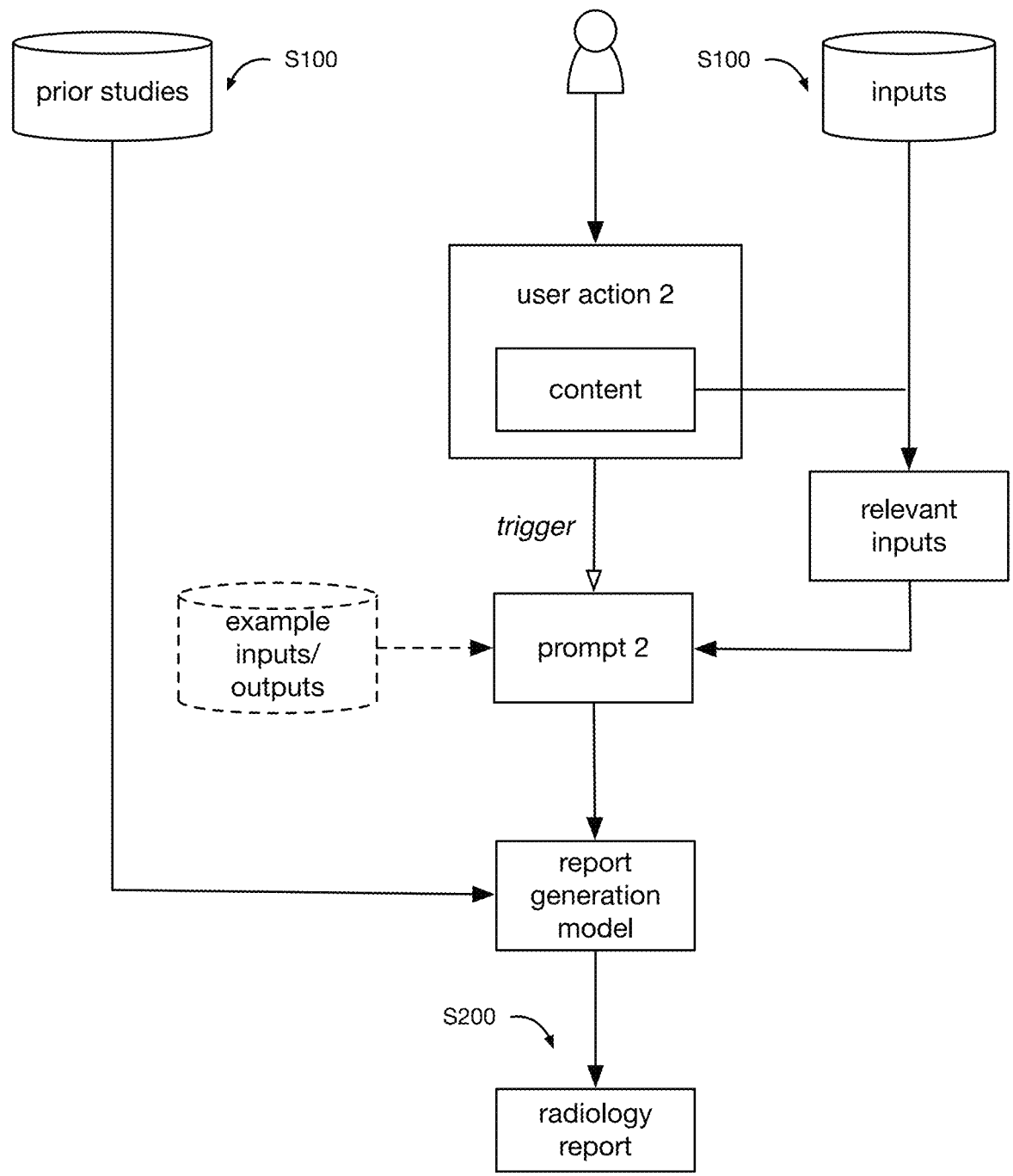

Prompts provided to the radiology report model can optionally include example inputs (e.g., a subset of templates, relevant findings, etc.) and expected outputs (e.g., a completed radiology report). Examples are shown in FIG. 4A and FIG. 4B. In a specific example, for generating the radiology report from dictated positive findings (e.g., without additional inputs), sample data can be generated by using a language model to summarize all or a portion of existing report data into relevant positive findings, wherein the summarization can be used for generating and/or tuning prompts.

Prompts can optionally be tuned (manually and/or automatically). In examples, iterative prompt expansion, self-evaluation, asking the report generation model to explain its reasoning, and/or any other prompt engineering method can be used. Additionally or alternatively, reinforcement learning, parameter-efficient fine-tuning (e.g., with LoRA and/or QLoRA), and/or any other fine tuning methods can be used to improve model performance. In a specific example, a combination of pretraining the report generation model on existing radiology report dataset(s) and parameter-efficient fine-tuning can be used.

The radiology report model preferably includes one or more language models (e.g., large language models) to generate the radiology report (e.g., radiology report text), but can additionally or alternatively include one or more multimodal models, foundation models, and/or be otherwise configured. The generated radiology report is preferably in a customized language (e.g., customized for the radiologist, the radiology group, the healthcare facility, etc.), but can alternatively be generalized and/or non-customized. Language customization is preferably speech engine-agnostic, but can alternatively not be speech engine-agnostic.

The language model(s) can be trained to output customized language. In a first example, a language model can be trained (e.g., pretrained) based on historical radiology reports (e.g., specific to the radiologist, the radiology group, etc.). In a second example, a language model can be trained by cohorting the radiologist into a group of similar radiologists (e.g., based on language usage in their historical or real-time radiology reports), and training the language model based on historical radiology reports associated with the cohort. The language model(s) can optionally be tuned and/or otherwise adjusted post-training (e.g., continuous learning, reinforcement learning, other machine learning techniques, etc.) to further improve customization over time. In a specific example, edits to the output text from a radiologist (e.g., before signing the final report; via S400) and/or feedback (e.g., comments, thumbs ups/thumbs down, etc.) can be used to tune the language model(s), for example via: reinforcement learning-based paradigms (e.g., Reinforcement Learning from Human Feedback (RLHF)), optimization-based paradigms (e.g., Direct Preference Optimization (DPO)), supervised fine-tuning (SFT) paradigms, model iteration, and/or any other suitable tuning models and/or paradigms. In examples, the radiology report model (e.g., an LLM-based radiology report model) can be fine-tuned for a particular: radiologist, radiology group, set of case information (e.g., pathology, imaging modality, etc.), and/or any other suitable parameter.

Additionally or alternatively, language customization can include determining (e.g., automatically recognizing or manually recognizing) each radiologist's and/or each radiology group's preferred preferences. In examples, the preferences can include: diction, syntax, verbosity, negation language, normal negative language for each different type of radiology report, template choices and report organization, description or incorporation of the clinical context, assessment of importance of various findings and the locations of their placement within the report text, description of each finding, repetition of findings, confident vs. hedging language uses, conditionality language uses, measurement language, comparison language, differential diagnoses, use of language for summarization or conclusions, follow-up recommendations, and/or any other radiologist-specific or radiology group-specific preferences. The preferences can optionally be used as input into the language model(s), to train (e.g., tune, adjust, etc.) the language model(s), and/or to further process or modify the results of the language model(s).

Language customization can optionally include analysis (e.g., automatic or manual) of each radiologist's and/or each radiology group's: word, phrase, sentence, or other text usages; word, phrase, sentence, or other text used in their templates or macros; prior reports (e.g., a subset similar to the current report and/or another subset of their prior reports); and/or any other associated information. This analysis and/or results from the analysis can optionally be used as input into the language model(s), to train (e.g., tune, adjust, etc.) the language model(s), and/or to further process or modify the results of the language model(s).

The radiology report can optionally be generated in response to a user action (e.g., voice command, hotkey press, clicks, button press, cursor navigation, separate window, trigger, user input, etc.) from a radiologist received at a user interface and/or otherwise received. User actions can optionally include content associated with one or more inputs. For example, the content can include inputs and/or identifiers to indicate inputs, wherein the content can be dictated, typed, and/or otherwise provided in association with the user action. Report generation parameters can optionally be determined based on the user action. Examples of report generation parameters can determine (e.g., select): report generation models (e.g., which models are used to generate the report), report generation model adjustments, inputs, prompts, and/or any other report generation process parameters. Examples are shown in FIG. 4A and FIG. 4B.

In a first specific example, a first user action (e.g., dictating "unchanged", pressing an "unchanged" button 42 within the input interface, a button click, a hotkey press, and/or any other command) can trigger generation of a radiology report, wherein all or most of the report is generated based on information in prior report(s) 45, with minimal or no significant changes relative to the prior report(s). An example is shown in FIG. 7. In an illustrative example, the findings in the prior report can be extracted and incorporated into the current report using the preferred style, template, formatting, and/or language (e.g., which can differ from the style, template, formatting, and/or language used in the prior report). Fields for specific inputs (e.g., clinical indication, comparison, study technique, contrast usage, radiation dose, etc.) within the radiology report can optionally be (automatically) updated.

Figure 9A:
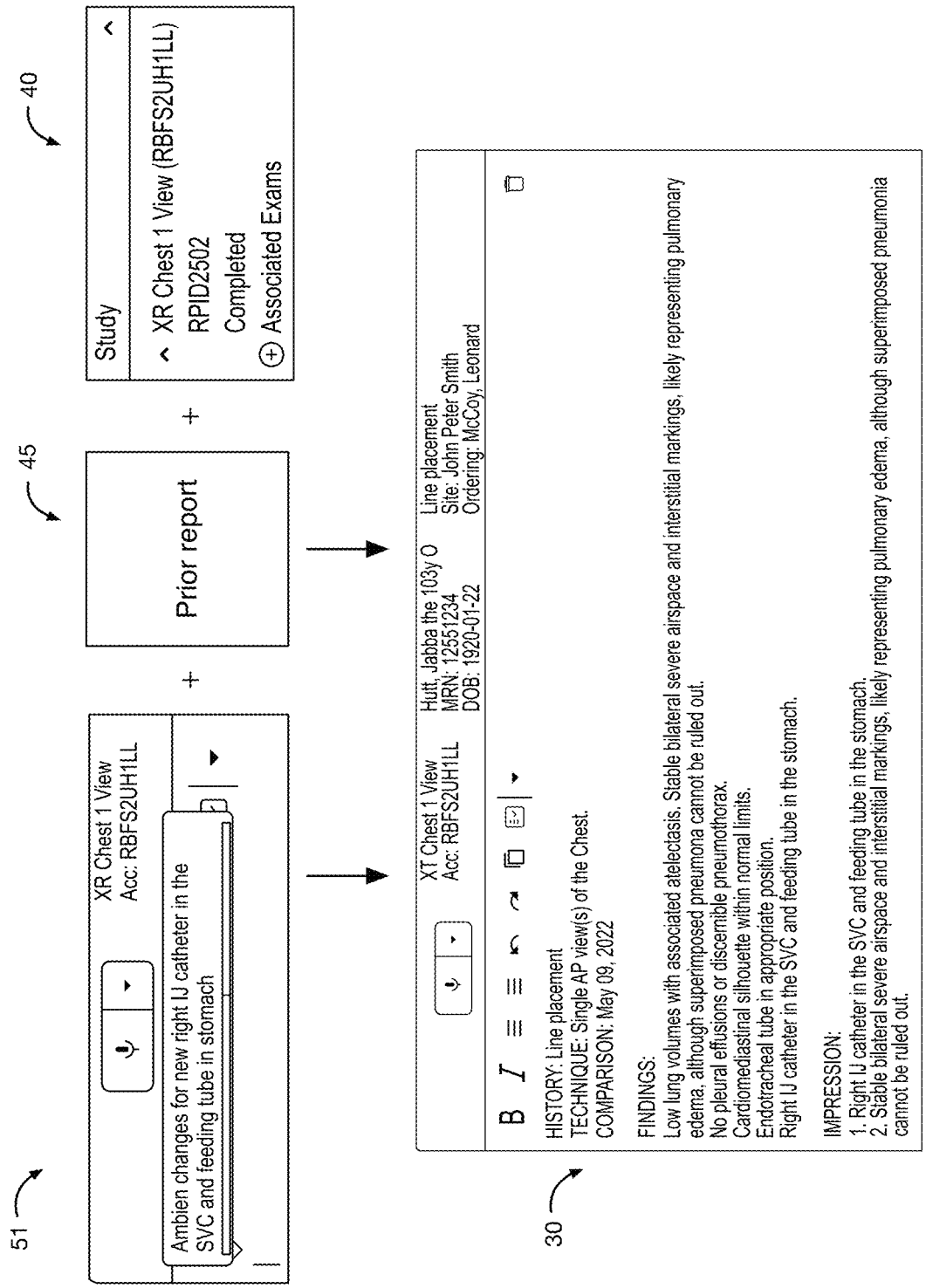
FIG. 9A depicts an illustrative example of generating a radiology report that is unchanged relative to a prior radiology report (the report in FIG. 9B) except for dictated findings.

In a second specific example, a second user action (e.g., dictating "unchanged except . . . ", a button click, a hotkey press, and/or any other command) that includes content associated with one or more inputs (e.g., findings and/or changes relative to one or more prior reports) can trigger generation of a radiology report, wherein all or most of the report is generated based on those inputs as well as information in prior report(s). An example of generating a predominately unchanged radiology report relative to a prior report (e.g., except for dictated changes) is shown in FIG. 9A (e.g., wherein the prior report is shown in FIG. 9B). In an illustrative example, the findings in the prior report can be extracted and incorporated into the current report using the preferred style, template, formatting, and/or language (e.g., which can differ from the style, template, formatting, and/or language used in the prior report). In a specific example, if the prior report was completed by a different radiologist, the prior findings can be incorporated into the current report in the specified style (e.g., the style of the current radiologist). Fields for specific inputs (e.g., measurements, findings, clinical indication, comparison, study technique, contrast usage, radiation dose information, recommendations, etc.) within the radiology report can optionally be (automatically) updated. Clinically insignificant and/or significant changes between the current and prior report can optionally be identified, wherein the changes can be highlighted separately (e.g., in the impression section of the report) and/or otherwise used.

In a third specific example, a third user action (e.g., dictating "generate report", opening a study, etc.) can trigger generation of a radiology report based on manual inputs (e.g., dictated findings) and/or any other inputs (e.g., generating a report from scratch). In an illustrative example, the inputs can be incorporated into the current report using the preferred style, template, formatting, and/or language. In a second illustrative example, the platform can pre-populate a full and/or a partial report upon the opening of a study (e.g., without and/or prior to any additional user action).

In examples, generating the radiology report can use systems and/or methods as described in U.S. application Ser. No. 18/207,880, filed 9 Jun. 2023, which is incorporated in its entirety by this reference.

However, the radiology report can be otherwise generated.

5.4 Post-Processing the Radiology Report S300

The method can optionally include post-processing the radiology report S300, which can function to: correct and/or flag model output errors (e.g., proof-read model outputs), further customize model outputs to individual radiologist user language (e.g., checking and/or improving language/style customization based on individual user word embeddings and/or use of subsets of the user's historical reports as additional model input), add consensus guideline-based recommendations, improve report language, ensure correct billing and adhere to national quality metrics, train one or more models, perform a summarization check, improve prompt injection protection, and/or otherwise improve the generated radiology report and/or the report generation model. In variants, S300 can be performed after S200, during S200, in response to S200, during S100, in response to S100, and/or at any other time. In examples, S300 can be performed at multiple times throughout the method (e.g., one or more times during S100, during S200, in response to each input received, etc.). In a specific example, S300 can include performing a plurality of error correction processes at multiple points throughout the method (e.g., the method can include one or more of: billing error handling, input error handling, report generation error handling, etc.).

The report generation model in S200 can optionally be chained with one or more post-processing language models (e.g., large language models) and/or other post-processing models: during report generation (e.g., within S200), after report generation (e.g., after S200; optionally in response to a user action), after receipt of an input (e.g., after S100), and/or at any other suitable time. In a specific example, chaining the models after report generation can increase the speed of the initial report generation. Additionally or alternatively, the radiologist can provide feedback (e.g., by selecting a list/menu of options, by typing feedback, etc.) after initial report generation, and a prompt can be determined based on the feedback. The prompt can be provided to the subsequent post-processing model(s) to improve the radiology report (e.g., in real time), and/or to tune one or more models (e.g., RLHF-based improvements).

Post-processing models can optionally perform any or all of: formatting an output (e.g., an impressions section); further improving language styling to better match a style preference (e.g., a of the radiologist, of another medical professional, etc.); modifying an output to conform with any quality metrics; checking and/or adjusting language for compliance with recommended and/or required language (e.g., medical classification lists such as the International Classification of Diseases and Related Health Problems [ICD], ICD-10, usage of word "indicates" for diagnoses to conform with billing guidelines and/or requirements, merit-based incentive payment system [MIPS] to help with and/or maximize reimbursement, etc.); notifying the radiologist of language which potentially may not conform with recommended and/or required language (e.g., as described above, so that the radiologist may manually edit, etc.); and/or any other processing. In specific examples, post-processing models can include any of the models described in U.S. patent application Ser. No. 17/020,593, filed 14 Sep. 2020, which is incorporated herein in its entirety by this reference.

In an example, the generated radiology report can be rerun (e.g., optionally alongside the original input data) through the same language model, a different language model, and/or any other model to look for errors (e.g., report generation errors). Examples of errors include: billing errors, input errors, report generation errors, and/or any other suitable errors. Examples of input errors can include: discrepancies between two or more sources of information, errors in the output of a findings model (e.g., errors in a speech to text operation), errors input by the radiologist, missing information (e.g., a finding from a previous exam for the patient a radiologist forgot to mention while completing a current radiology report for the patient), incorrect information, grammatical information, and/or any other errors. Examples of report generation errors include: contradictions within the generated outputs themselves; contradictions, hallucinations, and/or significant missed findings relative to the original input data; duplicated and/or partially duplicated concepts and/or sentences; incorrect language (e.g., gibberish boilerplate language); errors related to numbers, measurements, and/or dates; errors related to similar anatomical structures (different spine levels, different metacarpals or metatarsals, etc.); mixing and/or combining similar findings; findings with somewhat different severity levels are combined under a single severity level; speech recognition typos; grammatical and/or other language errors (e.g., punctuation); incorrect patient information (e.g., age, sex, medical history, etc.), and/or any other errors. Errors can be corrected, flagged, and/or otherwise addressed.

Additionally or alternatively, post-processing models can be used to identify errors within historical radiology report data (e.g., prior to using the historical radiology report data for model training) and/or discrepancies between historical radiology report data and current radiology report data. The historical radiology report data with errors and/or discrepancies can be corrected, flagged (e.g., radiology reports with errors are not used), and/or otherwise processed. Additionally or alternatively, post-processing models can be used to identify errors within an input (e.g., radiologist-dictated findings, prior report text, preferred user template, etc.) prior to using the input to generate the outputs, after generating outputs (e.g., when reviewing input compared to the radiology report for errors), and/or at any other time. In variants, post-processing can update one or more of the errors, or detect one or more errors and flag the error without directly updating the error (e.g., in the case that two data sources contain conflicting information that cannot be resolved without receiving additional input). Additionally or alternatively, post-processing models can be used to identify inconsistencies between language generated and a particular style (e.g., radiologist's style).

Post-processing models can be used to determine errors within a set of inputs determined at S100. Post-processing can include determining errors within an input received directly by the system. In a first example, post-processing models can be used to correct one or more errors made (e.g., typed) by the radiologist (e.g., in the input interface, in a field within the radiology template, etc.) while filling out the report. In a second example, post-processing models can be used to determine one or more errors within a set of case information (e.g., patient history, study information, billing information, etc.). Post-processing can include determining errors within a second set of inputs (e.g., a transcription) determined by the system based on a first set of inputs (e.g., radiologist audio) received by the system.

Post-processing models can be used to determine errors within a set of billing information. In examples, this can include any information used to submit a medical claim (e.g., to insurance) such as patient information, provider information, dates of service, diagnosis codes, procedure codes, modifiers, provider charges, insurance information, and/or any other suitable information. The post-processing models can scan for inconsistencies (e.g., between a received set of radiology images and a procedure code, between a finding and a diagnosis code, between a number of views received and a field indicating the number of views, between a body part included in the image and indicated in the radiology report, etc.), and optionally surface these to the radiologist and/or automatically correct the inconsistencies. As a common error in medical billing arises when there is a mismatch between the details of an order and the details indicated within a radiology report, automatically scanning for billing errors can confer the benefit of preventing errors that may lead to a procedure being improperly billed (e.g., an error that would yield in a rejection of a claim from an insurance company).

Optionally, determining errors can include determining that an input and/or an output matches (or doesn't match) a style and/or standard associated with a particular radiologist, radiology group, and/or other suitable entity. In examples, determining errors within a transcription of radiologist audio can: be performed with a model trained on that radiologist's historical radiology reports, include verifying the transcription against a corpus of that radiologist's historical radiology reports, determining a similarity score between the transcription and a style (e.g., style matrix) for the radiologist, and/or otherwise verifying the data.

However, the radiology report can be otherwise post-processed.

5.5 Adjusting the Radiology Report S400

The method can optionally include adjusting the radiology report S400, which can function to enable efficient radiologist editing, correct errors in the report, provide feedback to one or more models, and/or otherwise improve the current radiology report and/or the report generation process. S400 can be performed after S100, after S200, after S300, in response to a user action, in response to S100 (e.g., in response to receiving an input such as a finding dictated by a radiologist), automatically (e.g., zero-click), any time before or at the time of completion of the radiology report, and/or at any other time.

In examples, any adjustment can be made automatically, displayed (e.g., as suggestions, notifications, highlights, etc.), and/or otherwise implemented. In specific examples, the adjustments can be displayed as highlighting of "out-of-place" or incorrect words, phrases, sentences, or other text in a user interface of the reporting platform. Displayed adjustments can optionally be associated with a user action (e.g., button press, notification acceptance, etc.) that can accept (or dismiss) the adjustment. In a specific example, the user interface can provide one or more options for correct words, phrases, sentences, or other text for each adjustment.

A user can optionally input one or more instructions for adjusting the report (e.g., wherein the adjustments are determined and/or implemented using the same report generation model in S200 or a different model). In examples, instructions can include: adding or removing text from all or a portion of the radiology report (e.g., the impression section), checking for inconsistencies, making the report more concise and/or confident, and/or any other adjustment instructions. The instructions can be input using dictation, typing, selecting one or more instructions from a list (e.g., the most commonly used instructions for all users and/or for that user), and/or any other input method.

Figure 5:
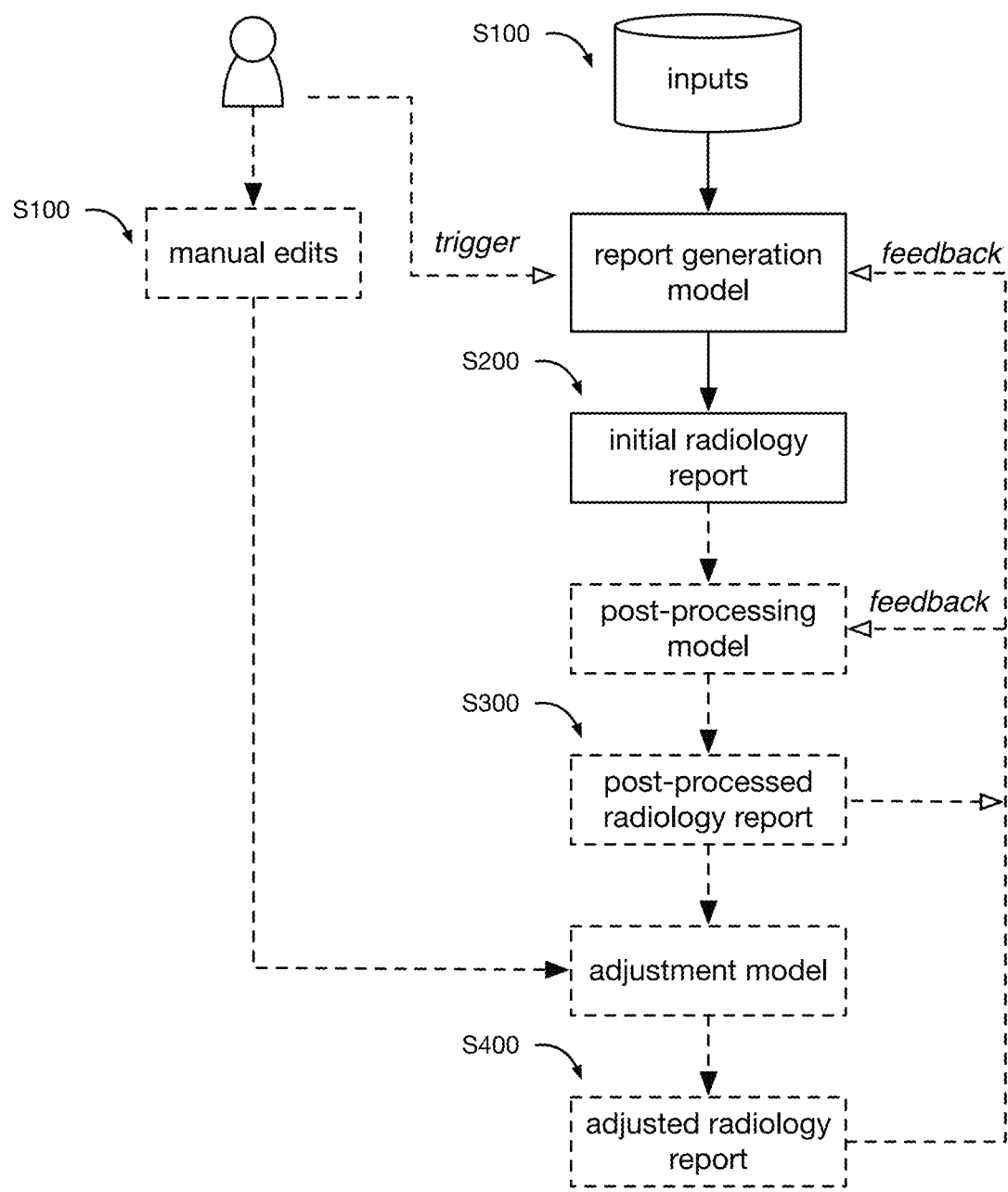
FIG. 5 depicts an example of post-processing a radiology report and adjusting the radiology report.

In a first variant, adjusting the radiology report includes a radiologist manually editing the report. An example is shown in FIG. 5. For example, the radiologist can insert one or more inputs into the radiology report (after a template has been inserted, after the report has been generated, etc.), wherein the radiologist can manually select the location to insert the inputs, or the location can be automatically determined. In a specific example, the radiologist dictates a finding, wherein the report generation model inserts the finding into the correct location (using S200 methods). The manual edits can optionally include feedback (e.g., as described in S300) for one or more models.

In a second variant, adjusting the radiology report includes automatically determining adjustments for the report. Adjusting the radiology report can optionally include reviewing (e.g., checking) the report, and automatically determining adjustments based on the review (e.g., based on errors identified in the review). The review can evaluate: inclusion of clinical concepts, inclusion of body structures, negative language, contradictory language, and/or any other text in the radiology report. The review can be based on patient information, national best practices and/or consensus guidelines, quality measure reporting requirements, preferences (e.g., of the radiologist, the ordering provider, the radiology group, the healthcare facility, etc.), disease staging guidelines, billing requirements or language related to billing-related elements (e.g., diagnosis, finding, symptom, medical service, procedure codes, etc.), quality guidelines and/or measures, and/or any other inputs. However, adjustments can be determined without a review.

The adjustments can include adjustment (e.g., addition, removal, and/or modification) of: any radiology report text (e.g., based on a review of the report), pertinent negative language (e.g., pertinent negative findings), contradictory language (e.g., internally contradictory language, language that contradicts with another report or a current finding, etc.), existing language in the radiology report made unnecessary by inputs (e.g., findings dictated by the radiologist), radiologist inputs (e.g., to ensure accuracy or clinical appropriateness for the insertion location), any other text, and/or any other text adjustments. In an example, the template inserted in the radiology report can include negative language (e.g., most or all sections are baseline "normal negative"); when the radiologist dictates a positive finding (e.g., "pneumothorax"), adjustments to language in the template are determined (e.g., "no evidence of pneumothorax" is removed, other pertinent language such as pneumothorax size appears, etc.). Errors in the report (e.g., contradictory language, unnecessary language, etc.) and/or adjustments to the report can be determined using one or more models (e.g., the same report generation model in S200 or a different model). Ontologies, hyponyms, embeddings, and/or other techniques can optionally be used with the one or more models to assist in identifying errors.

In a third variant, adjusting the radiology report can include automatically adjusting generated text results from a speech-to-text engine (e.g., in the reporting platform). The adjustment can occur: immediately after the generation of report text results by the speech-to-text engine prior to its appearance in the reporting editor (e.g., in near-real time with dictation), after the appearance of the text in the reporting editor, at time of completion of the report (e.g., initiated automatically or manually), and/or at any other time. In an example, a speech correction model (e.g., a machine learning model) can output corrected text based on the text results from the speech-to-text engine and optionally other inputs, including: the vocabulary that the individual radiologist and/or associated radiology group most commonly uses, study information, radiology report information, the specific section of the report that the radiologist is currently dictating, the context of the surrounding text in the report, patient information, location, other factors or preferences specific to the radiologist or the radiology group, and/or any other inputs. The speech correction model can optionally be customized to each individual radiologist or radiology group (e.g., trained using historical radiology reports for the individual radiologist or radiology group).

Manual or automatic radiology report adjustments (e.g., from any variant) can optionally trigger updates to one or more databases (e.g., updates templates, updated macros, etc.), retraining of one or more models (based on the adjustments), and/or any other downstream processes.

However, the radiology report can be otherwise adjusted.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

We claim:

1. A method for automatically generating a radiology report for a radiologist, comprising:
  with a computing system comprising model architecture configured for natural language processing, generating more than 75% of the radiology report upon:
    receiving a first set of inputs associated with a patient at the computing system;
    with an input determination model of the computing system, determining a report template based on the first set of inputs, wherein determining the report template comprises returning a ranked list of templates based upon a procedure type, an imaging modality, a patient demographic, and a study location, represented in the first set of inputs, wherein the input determination model comprises a large language model (LLM) combined with a semantic search engine;
    receiving a set of unstructured findings, comprising at least one of an audio data stream and text data in free-text form, associated with the patient;
    based on the set of unstructured findings and the first set of inputs, using a set of trained models of the computing system, automatically generating a set of text to populate a plurality of fields of the report template, wherein the set of text is generated with a writing style represented in word embeddings generated from historical reports of the radiologist; and
    processing the report template after populating the plurality of fields, wherein processing the report template comprises correcting errors in the report template based upon inconsistencies between the report template and historical radiology report data for the radiologist in the writing style of the radiologist, upon checking word embeddings in the populated report template and in historical reports of the radiologist; and performing a billing error correction procedure, comprising:
      determining predicted billing information based on a number of radiology image views provided with the set of inputs,
      comparing the number of radiology image views with a field indicating number of views in the report template, and if the number of radiology image views does not match the field, correcting at least one of the predicted billing information and the report template.

2. The method of claim 1, wherein automatically generating the set of text comprises:
   determining a set of topics within the set of text;
   organizing each of the set of topics into a respective field of the plurality of fields;
   predicting additional text to accompany the topics within the respective fields.

3. The method of claim 1, further comprising:
   receiving the set of unstructured findings as audio through a voice interface; and
   converting the audio to written text, comprising, with a second set of trained models, determining a set of macros based on the audio and a corpus of historical reports generated by the radiologist.

4. The method of claim 1, wherein determining the report template based on a set of metadata comprises:
   using a second set of trained models, predicting a set of most likely report templates;
   presenting the set of most likely report templates at a radiologist interface; and
   receiving a selection of the report template from the radiologist.

5. The method of claim 4, further comprising retraining the second set of trained models based on the selection.

6. The method of claim 1, wherein the plurality of fields of the report belong to a findings section of the radiology report, wherein the method further comprises, using a second set of trained models, automatically generating an impression section of the radiology report based on the generated set of text populating the plurality of fields of the report template.

7. The method of claim 1, wherein the method further comprises automatically determining a set of findings from the imagery using a set of trained models comprising at least one of: computer vision models or multimodal models.

8. The method of claim 1, wherein the set of metadata comprises a radiologist identifier of a radiologist writing the report.

9. The method of claim 1, wherein the set of medical information comprises medical imagery.

10. A method for automatically generating a medical document, comprising:
    with a computing system comprising model architecture configured for natural language processing:
      receiving a set of medical information associated with a patient, at the computing system;
      receiving a first set of unstructured input, comprising an audio data stream, from a medical professional, at the computing system;
      based on the first set of unstructured input and the set of medical information, using a first set of trained models comprising a large language model (LLM) combined with a semantic search engine, automatically generating a set of text to populate a plurality of fields of the medical document;
      receiving a second set of unstructured input, comprising text data in free-text form, from the medical professional, at the computing system;
      based on the second set of unstructured input, using a second set of trained models, automatically updating at least one of the plurality of fields of the medical document;
      processing the medical document after updating the plurality of fields, wherein processing the report template comprises correcting errors in the medical document based upon inconsistencies between the medical document and historical radiology report data for the medical professional in the writing style of the medical professional, upon checking word embeddings in the processed medical document and in historical reports of the medical professional; and
      performing a billing error correction procedure, comprising:
        determining predicted billing information based on a number of radiology image views provided with the set of inputs,
        comparing the number of radiology image views with a field indicating number of views in the report template, and
        if the number of radiology image views does not match the field, correcting at least one of the predicted billing information and the report template.

11. The method of claim 10, further comprising determining a template of the medical document based on: an identifier associated with the medical professional and the set of medical information associated with a patient, wherein the set of medical information associated with the patient comprises a set of imagery and a set of medical history.

12. The method of claim 10, wherein the first set of unstructured input comprises unstructured audio, wherein automatically generating the set of text to populate the plurality of fields of the medical document comprises:
    transcribing the unstructured audio to unstructured text using a set of transcription models;
    determining an error within the unstructured text; and
    predicting a set of corrections to the error using a set of error models.

13. The method of claim 12, wherein predicting the set of corrections comprises comparing a subset of the text containing the error to a medical corpus.

14. The method of claim 13, wherein the medical corpus comprises historical text generated by the medical professional.

15. The method of claim 12, further comprising displaying the predicted set of corrections to the medical professional for acceptance or rejection.

16. The method of claim 10, wherein automatically generating the set of text to populate the plurality of fields of the medical document comprises:
    determining a set of topics within the set of text;
    organizing each of the set of topics into a respective field of the plurality of fields;
    predicting additional text to accompany the topics within the respective fields.

17. The method of claim 10, wherein the set of text is generated with the writing style of the medical professional.

18. The method of claim 10, further comprising displaying a chatbot at a graphical user interface, wherein the second set of unstructured input comprises text typed into a text box associated with the chatbot.

* * * * *